US012582816B2

(12) United States Patent
Dahl et al.

(10) Patent No.: US 12,582,816 B2
(45) Date of Patent: Mar. 24, 2026

(54) SYSTEMS AND METHODS FOR EXTRACTING AN ELECTRODE LEAD

(71) Applicant: Mainstay Medical Limited, County Dublin (IE)

(72) Inventors: Michael Dahl, Eden Prairie, MN (US); Jason Skubitz, Arden Hills, MN (US)

(73) Assignee: Mainstay Medical Limited, Dublin (IE)

( * ) Notice: Subject to any disclaimer, the term of this patent is extended or adjusted under 35 U.S.C. 154(b) by 457 days.

(21) Appl. No.: 18/186,149

(22) Filed: Mar. 18, 2023

(65) Prior Publication Data

US 2023/0302274 A1     Sep. 28, 2023

Related U.S. Application Data

(60) Provisional application No. 63/269,756, filed on Mar. 22, 2022.

(51) Int. Cl.
*A61N 1/05*          (2006.01)
*A61B 17/16*        (2006.01)
*A61M 29/02*       (2006.01)

(52) U.S. Cl.
CPC ........ *A61N 1/0558* (2013.01); *A61B 17/1671* (2013.01); *A61M 29/02* (2013.01); *A61M 2210/1003* (2013.01)

(58) Field of Classification Search
CPC ......... A61N 2001/0578; A61N 1/0558; A61M 2210/1003; A61M 29/02; A61B 17/32053; A61B 17/1671

(Continued)

(56) References Cited

U.S. PATENT DOCUMENTS

| | | | |
|---|---|---|---|
| 1,526,595 A | 2/1925 | George et al. | |
| 3,077,884 A | 2/1963 | John et al. | |

(Continued)

FOREIGN PATENT DOCUMENTS

| | | |
|---|---|---|
| CN | 1211930 A | 3/1999 |
| CN | 1211930 C | 7/2005 |

(Continued)

OTHER PUBLICATIONS

U.S. Appl. No. 12/075,174 / U.S. Pat. No. 8,428,728, filed Mar. 10, 2008 / Apr. 23, 2013.

(Continued)

*Primary Examiner* — Jocelin C Tanner
(74) *Attorney, Agent, or Firm* — Greenberg Traurig, LLP; Christopher C. Bolten; Albert K. Heng

(57) ABSTRACT

Systems and methods are provided for extracting an implanted lead from a patient's body. The system may include a dilator and a trephine for extracting the electrode lead. A sheath may be included that is advanced over the proximal end of an electrode lead until the distal end of the sheath abuts a collar of the electrode lead coupled to proximal fixation elements. The dilator may be rotatably and axially advanced over the sheath until the distal end of the dilator collapses the proximal fixation elements within a lumen of the dilator. The trephine may then be rotatably and axially advanced over the dilator such that a cutting edge of the trephine cuts tissue surrounding distal fixation elements of the electrode lead to thereby dislodge the electrode lead.

26 Claims, 16 Drawing Sheets

(58) Field of Classification Search
USPC ......................................................... 606/129
See application file for complete search history.

(56) References Cited

U.S. PATENT DOCUMENTS

| | | | |
|---|---|---|---|
| 3,416,534 A | 12/1968 | Quinn | |
| 3,710,777 A | 1/1973 | Sparks | |
| 3,754,555 A | 8/1973 | Schmitt | |
| 3,875,947 A | 4/1975 | Jula et al. | |
| 3,893,463 A | 7/1975 | Williams | |
| 3,902,501 A | 9/1975 | Citron et al. | |
| 3,976,082 A | 8/1976 | Schmitt | |
| 3,999,551 A | 12/1976 | Spitz et al. | |
| 4,010,757 A | 3/1977 | Jula et al. | |
| 4,026,301 A | 5/1977 | Friedman et al. | |
| 4,031,899 A | 6/1977 | Renirie | |
| 4,149,528 A | 4/1979 | Murphy | |
| 4,235,246 A | 11/1980 | Weiss | |
| 4,269,198 A | 5/1981 | Stokes | |
| 4,342,317 A | 8/1982 | Axelgaard | |
| 4,408,609 A | 10/1983 | Axelgaard | |
| 4,418,693 A | 12/1983 | LeVeen et al. | |
| 4,471,777 A | 9/1984 | McCorkle, Jr. | |
| 4,528,984 A | 7/1985 | Morawetz et al. | |
| 4,549,556 A | 10/1985 | Tarjan et al. | |
| 4,574,806 A | 3/1986 | McCarthy | |
| 4,608,986 A | 9/1986 | Beranek et al. | |
| 4,658,835 A | 4/1987 | Pohndorf | |
| 4,696,308 A * | 9/1987 | Meller | A61B 17/1668 |
| | | | 73/864.45 |
| 4,832,687 A | 5/1989 | Smith, III | |
| 4,863,430 A * | 9/1989 | Klyce | A61M 39/0613 |
| | | | 604/170.03 |
| 4,917,093 A | 4/1990 | Dufresne et al. | |
| 5,069,680 A | 12/1991 | Grandjean | |
| 5,199,430 A | 4/1993 | Fang et al. | |
| 5,215,088 A | 6/1993 | Normann et al. | |
| 5,273,053 A | 12/1993 | Pohndorf | |
| 5,300,108 A | 4/1994 | Rebell et al. | |
| 5,330,515 A | 7/1994 | Rutecki et al. | |
| 5,376,108 A | 12/1994 | Collins et al. | |
| 5,496,345 A | 3/1996 | Kieturakis et al. | |
| 5,501,452 A | 3/1996 | Halvorson | |
| 5,507,788 A | 4/1996 | Lieber | |
| 5,522,854 A | 6/1996 | Ideker et al. | |
| 5,569,183 A | 10/1996 | Kieturakis | |
| 5,575,797 A | 11/1996 | Neubauer et al. | |
| 5,638,825 A | 6/1997 | Yamazaki et al. | |
| 5,651,781 A | 7/1997 | Grace | |
| 5,733,307 A | 3/1998 | Dinsdale | |
| 5,741,321 A | 4/1998 | Brennen | |
| 5,760,341 A | 6/1998 | Laske et al. | |
| 5,782,841 A | 7/1998 | Ritz et al. | |
| 5,807,234 A | 9/1998 | Bui et al. | |
| 5,873,900 A | 2/1999 | Maurer et al. | |
| 5,897,584 A | 4/1999 | Herman | |
| 5,906,612 A * | 5/1999 | Chinn | A61B 18/02 |
| | | | 606/23 |
| 5,916,172 A | 6/1999 | Hodges et al. | |
| 5,957,968 A | 9/1999 | Belden et al. | |
| 5,980,515 A | 11/1999 | Tu | |
| 6,104,957 A | 8/2000 | Alo et al. | |
| 6,119,516 A | 9/2000 | Hock | |
| 6,314,325 B1 | 11/2001 | Fitz | |
| 6,319,241 B1 | 11/2001 | King et al. | |
| 6,324,414 B1 | 11/2001 | Gibbons et al. | |
| 6,366,819 B1 | 4/2002 | Stokes | |
| 6,381,496 B1 | 4/2002 | Meadows et al. | |
| 6,406,421 B1 | 6/2002 | Grandjean et al. | |
| 6,451,036 B1 | 9/2002 | Heitzmann et al. | |
| 6,473,654 B1 | 10/2002 | Chinn | |
| 6,516,227 B1 | 2/2003 | Meadows et al. | |
| 6,527,787 B1 | 3/2003 | Fogarty et al. | |
| 6,565,594 B1 | 5/2003 | Herweck et al. | |
| 6,600,954 B2 | 7/2003 | Cohen et al. | |
| 6,600,956 B2 | 7/2003 | Maschino et al. | |
| 6,605,094 B1 | 8/2003 | Mann et al. | |
| 6,671,557 B1 | 12/2003 | Gliner | |
| 6,735,474 B1 | 5/2004 | Loeb et al. | |
| 6,839,594 B2 | 1/2005 | Cohen et al. | |
| 6,845,271 B2 | 1/2005 | Fang et al. | |
| 6,862,479 B1 | 3/2005 | Whitehurst et al. | |
| 6,971,393 B1 | 12/2005 | Mamo et al. | |
| 7,018,384 B2 | 3/2006 | Skakoon | |
| 7,096,070 B1 | 8/2006 | Jenkins et al. | |
| 7,206,641 B2 | 4/2007 | Ignagni et al. | |
| 7,218,970 B2 | 5/2007 | Ley et al. | |
| 7,239,918 B2 | 7/2007 | Strother et al. | |
| 7,286,879 B2 | 10/2007 | Wallace | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,337,005 B2 | 2/2008 | Kim et al. | |
| 7,337,006 B2 | 2/2008 | Kim et al. | |
| 7,369,894 B2 | 5/2008 | Gerber | |
| 7,389,149 B2 | 6/2008 | Rossing et al. | |
| 7,444,181 B2 | 10/2008 | Shi et al. | |
| 7,447,546 B2 | 11/2008 | Kim et al. | |
| 7,450,993 B2 | 11/2008 | Kim et al. | |
| 7,489,561 B2 | 2/2009 | Armstrong et al. | |
| 7,493,175 B2 | 2/2009 | Cates et al. | |
| 7,499,746 B2 | 3/2009 | Buhlmann et al. | |
| 7,502,651 B2 | 3/2009 | Kim et al. | |
| 7,515,971 B1 | 4/2009 | Doan | |
| 7,553,313 B2 | 6/2009 | Bagby | |
| 7,580,753 B2 | 8/2009 | Kim et al. | |
| 7,668,598 B2 | 2/2010 | Herregraven et al. | |
| 7,684,866 B2 | 3/2010 | Fowler et al. | |
| 7,708,763 B2 | 5/2010 | Selover et al. | |
| 7,761,166 B2 | 7/2010 | Giftakis et al. | |
| 7,792,591 B2 | 9/2010 | Rooney et al. | |
| 7,797,053 B2 | 9/2010 | Atkinson et al. | |
| 7,813,803 B2 | 10/2010 | Heruth et al. | |
| 7,908,015 B2 | 3/2011 | Lazeroms et al. | |
| 7,917,230 B2 | 3/2011 | Bly | |
| 7,930,039 B2 | 4/2011 | Olson | |
| 7,981,144 B2 | 7/2011 | Geist et al. | |
| 8,016,846 B2 | 9/2011 | McFarlin et al. | |
| 8,065,020 B2 | 11/2011 | Ley et al. | |
| 8,082,039 B2 | 12/2011 | Kim et al. | |
| 8,170,690 B2 | 5/2012 | Morgan et al. | |
| 8,229,565 B2 | 7/2012 | Kim et al. | |
| 8,229,656 B2 | 7/2012 | Ikushima et al. | |
| 8,249,701 B2 | 8/2012 | Imran et al. | |
| 8,249,713 B2 | 8/2012 | Fang et al. | |
| 8,321,021 B2 | 11/2012 | Kisker et al. | |
| 8,380,318 B2 | 2/2013 | Kishawi et al. | |
| 8,386,045 B2 | 2/2013 | Zhao et al. | |
| 8,391,966 B2 | 3/2013 | Luo et al. | |
| 8,409,233 B1 | 4/2013 | Chinn et al. | |
| 8,428,728 B2 | 4/2013 | Sachs | |
| 8,463,383 B2 | 6/2013 | Sakai et al. | |
| 8,498,697 B2 | 7/2013 | Yong et al. | |
| 8,606,358 B2 | 12/2013 | Sachs | |
| 8,798,005 B1 | 8/2014 | Vargantwar et al. | |
| 8,886,337 B2 | 11/2014 | Bennett et al. | |
| 8,965,516 B2 | 2/2015 | Bennett et al. | |
| 9,072,897 B2 | 7/2015 | Sachs et al. | |
| 9,079,019 B2 | 7/2015 | Crosby et al. | |
| 9,108,053 B2 | 8/2015 | Crosby et al. | |
| 9,186,501 B2 | 11/2015 | Rawat et al. | |
| 9,248,278 B2 | 2/2016 | Crosby et al. | |
| 9,320,847 B2 | 4/2016 | Rooney et al. | |
| 9,339,269 B2 | 5/2016 | Geistert | |
| 9,474,906 B2 | 10/2016 | Sachs et al. | |
| 9,561,364 B2 | 2/2017 | Bondhus et al. | |
| 9,586,041 B2 | 3/2017 | Goode et al. | |
| 9,649,490 B2 | 5/2017 | Booker | |
| 9,861,811 B2 | 1/2018 | Crosby et al. | |
| 9,889,294 B2 | 2/2018 | Kalmann et al. | |
| 9,950,159 B2 | 4/2018 | Beck et al. | |
| 9,981,122 B2 | 5/2018 | Rawat et al. | |
| 9,999,763 B2 | 6/2018 | Shiroff et al. | |
| 10,016,603 B2 | 7/2018 | Sachs et al. | |

(56) References Cited

U.S. PATENT DOCUMENTS

| | | |
|---|---|---|
| 10,195,419 B2 | 2/2019 | Shiroff et al. |
| 10,327,810 B2 | 6/2019 | Shiroff et al. |
| 10,448,999 B2 | 10/2019 | Schneider |
| 10,449,355 B2 | 10/2019 | Beck et al. |
| 10,471,268 B2 | 11/2019 | Crosby et al. |
| 10,653,440 B2 | 5/2020 | Goode et al. |
| 10,661,078 B2 | 5/2020 | Crosby et al. |
| 10,729,415 B2 | 8/2020 | Roeder et al. |
| 10,828,490 B2 | 11/2020 | Sachs et al. |
| 11,103,706 B2 | 8/2021 | Sachs et al. |
| 11,331,488 B2 | 5/2022 | Sachs et al. |
| 11,376,427 B2 | 7/2022 | Beck et al. |
| 11,406,421 B2 | 8/2022 | Shiroff et al. |
| 11,471,670 B2 | 10/2022 | Crosby et al. |
| 11,679,261 B2 | 6/2023 | Sachs et al. |
| 11,679,262 B2 | 6/2023 | Sachs et al. |
| 11,684,774 B2 | 6/2023 | Crosby |
| 11,937,847 B2 | 3/2024 | Shiroff et al. |
| 11,951,310 B2 | 4/2024 | Sachs et al. |
| 12,048,844 B2 | 7/2024 | Crosby et al. |
| 12,121,728 B2 | 10/2024 | Sachs et al. |
| 12,168,130 B2 | 12/2024 | Sachs et al. |
| 12,285,612 B1 | 4/2025 | Sachs et al. |
| 12,458,802 B2 | 11/2025 | Sachs et al. |
| 2001/0053885 A1 | 12/2001 | Gielen et al. |
| 2002/0065543 A1 | 5/2002 | Gomperz et al. |
| 2002/0068960 A1 | 6/2002 | Saberski et al. |
| 2002/0099419 A1 | 7/2002 | Cohen et al. |
| 2002/0115945 A1 | 8/2002 | Herman et al. |
| 2002/0147485 A1 | 10/2002 | Mamo et al. |
| 2002/0156513 A1 | 10/2002 | Borkan |
| 2002/0161415 A1 | 10/2002 | Cohen et al. |
| 2002/0183765 A1 | 12/2002 | Adams |
| 2003/0100933 A1 | 5/2003 | Ayal et al. |
| 2003/0120323 A1 | 6/2003 | Meadows et al. |
| 2003/0120328 A1 | 6/2003 | Jenkins et al. |
| 2003/0135120 A1 | 7/2003 | Parks et al. |
| 2003/0199938 A1 | 10/2003 | Smits et al. |
| 2003/0204228 A1 | 10/2003 | Cross et al. |
| 2004/0030360 A1 | 2/2004 | Eini et al. |
| 2004/0097986 A1 | 5/2004 | Adams |
| 2004/0111118 A1 | 6/2004 | Hill et al. |
| 2004/0122482 A1 | 6/2004 | Tung et al. |
| 2004/0147969 A1 | 7/2004 | Mann et al. |
| 2004/0167580 A1 | 8/2004 | Mann et al. |
| 2004/0214790 A1 | 10/2004 | Borgens |
| 2004/0230281 A1 | 11/2004 | Heil et al. |
| 2004/0236383 A1 | 11/2004 | Yelizarov |
| 2005/0070971 A1 | 3/2005 | Fowler et al. |
| 2005/0075701 A1 | 4/2005 | Shafer |
| 2005/0080472 A1 | 4/2005 | Atkinson et al. |
| 2005/0107861 A1 | 5/2005 | Harris et al. |
| 2005/0119713 A1 | 6/2005 | Whitehurst et al. |
| 2005/0137644 A1 | 6/2005 | Boveja et al. |
| 2005/0149154 A1 | 7/2005 | Cohen et al. |
| 2005/0154389 A1 | 7/2005 | Selover et al. |
| 2005/0165456 A1 | 7/2005 | Mann et al. |
| 2005/0171551 A1* | 8/2005 | Sukovich .......... A61B 17/0218 |
| | | 606/86 R |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2005/0288730 A1 | 12/2005 | Deem et al. |
| 2006/0004429 A1 | 1/2006 | Mrva et al. |
| 2006/0009810 A1 | 1/2006 | Mann et al. |
| 2006/0009827 A1 | 1/2006 | Kurth et al. |
| 2006/0032657 A1 | 2/2006 | Zarembo |
| 2006/0052856 A1 | 3/2006 | Kim et al. |
| 2006/0074456 A1 | 4/2006 | Pyles et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0155341 A1 | 7/2006 | Tehrani et al. |
| 2006/0184222 A1 | 8/2006 | Camps et al. |
| 2006/0206166 A1 | 9/2006 | Weiner |
| 2006/0235484 A1 | 10/2006 | Jaax et al. |
| 2006/0241716 A1 | 10/2006 | Finch et al. |
| 2006/0259074 A1 | 11/2006 | Kelleher et al. |
| 2006/0293662 A1 | 12/2006 | Boyer et al. |
| 2007/0027501 A1 | 2/2007 | Jensen et al. |
| 2007/0049980 A1 | 3/2007 | Zielinski et al. |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1 | 5/2007 | Bonde |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1 | 10/2007 | Mann et al. |
| 2007/0239224 A1 | 10/2007 | Bennett et al. |
| 2007/0276453 A1 | 11/2007 | Hill et al. |
| 2008/0026981 A1 | 1/2008 | Muhrer et al. |
| 2008/0027505 A1 | 1/2008 | Levin et al. |
| 2008/0103570 A1 | 5/2008 | Gerber |
| 2008/0103573 A1 | 5/2008 | Gerber |
| 2008/0103574 A1 | 5/2008 | Gerber |
| 2008/0103579 A1 | 5/2008 | Gerber |
| 2008/0132961 A1 | 6/2008 | Jaax et al. |
| 2008/0132969 A1 | 6/2008 | Bennett et al. |
| 2008/0147156 A1 | 6/2008 | Imran |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1 | 9/2008 | Sachs |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1 | 1/2009 | Binmoeller |
| 2009/0020764 A1 | 1/2009 | Anderson et al. |
| 2009/0105700 A1 | 4/2009 | Anderson |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0248095 A1 | 10/2009 | Schleicher et al. |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0299444 A1 | 12/2009 | Boling |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2010/0331883 A1 | 12/2010 | Schmitz et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1 | 6/2011 | Ravikumar et al. |
| 2011/0190786 A1 | 8/2011 | Gerber et al. |
| 2011/0202112 A1 | 8/2011 | Ruais |
| 2011/0224665 A1 | 9/2011 | Crosby et al. |

(56) References Cited

U.S. PATENT DOCUMENTS

| | | |
|---|---|---|
| 2011/0224682 A1 | 9/2011 | Westlund et al. |
| 2011/0251662 A1 | 10/2011 | Griswold et al. |
| 2011/0257660 A1 | 10/2011 | Jones et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0209285 A1 | 8/2012 | Barker et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0053926 A1 | 2/2013 | Hincapie Ordonez et al. |
| 2013/0096641 A1 | 4/2013 | Strother et al. |
| 2013/0105071 A1 | 5/2013 | Digiore et al. |
| 2013/0106347 A1 | 5/2013 | Kallmyer et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0218247 A1 | 8/2013 | Sachs |
| 2013/0238066 A1 | 9/2013 | Boggs, II et al. |
| 2013/0245715 A1 | 9/2013 | Peterson |
| 2013/0253605 A1 | 9/2013 | Bennett et al. |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2013/0338730 A1 | 12/2013 | Shiroff et al. |
| 2014/0029695 A1 | 1/2014 | Liu et al. |
| 2014/0031837 A1 | 1/2014 | Perryman et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0114385 A1 | 4/2014 | Nijhuis et al. |
| 2014/0277022 A1* | 9/2014 | Perrin ................ A61B 17/3209 |
| | | 606/167 |
| 2014/0288616 A1 | 9/2014 | Rawat et al. |
| 2014/0350653 A1 | 11/2014 | Shiroff et al. |
| 2015/0101188 A1 | 4/2015 | Klardie et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |
| 2016/0310732 A1 | 10/2016 | Beck et al. |
| 2017/0100408 A1 | 4/2017 | Bertolini et al. |
| 2018/0008311 A1* | 1/2018 | Shiroff ................ A61N 1/0558 |
| 2018/0133461 A1 | 5/2018 | Crosby et al. |
| 2018/0256906 A1 | 9/2018 | Pivonka et al. |
| 2018/0353757 A1 | 12/2018 | Sachs et al. |
| 2019/0167995 A1 | 6/2019 | Sachs et al. |
| 2019/0328423 A1 | 10/2019 | Shiroff et al. |
| 2020/0203858 A1 | 6/2020 | Youtsey |
| 2025/0249252 A1 | 8/2025 | Sachs et al. |

FOREIGN PATENT DOCUMENTS

| | | |
|---|---|---|
| CN | 101678203 A | 3/2010 |
| EP | 0587269 A2 | 3/1994 |
| EP | 0587269 B1 | 12/1998 |
| EP | 1053762 A2 | 11/2000 |
| EP | 1255583 A1 | 11/2002 |
| EP | 1053762 B1 | 8/2005 |
| EP | 1255583 B1 | 12/2007 |
| EP | 2125100 A1 | 12/2009 |
| EP | 2273931 A2 | 1/2011 |
| WO | WO-0158520 A1 | 8/2001 |
| WO | WO-2004066820 A2 | 8/2004 |
| WO | WO-2006091611 A1 | 8/2006 |
| WO | WO-2006133445 A2 | 12/2006 |
| WO | WO-2006135791 A2 | 12/2006 |
| WO | WO-2007047954 A2 | 4/2007 |
| WO | WO-2007051146 A1 | 5/2007 |
| WO | WO-2007138598 A2 | 12/2007 |
| WO | WO-2008048471 A2 | 4/2008 |
| WO | WO-2008070807 A2 | 6/2008 |
| WO | WO-2008094952 A2 | 8/2008 |
| WO | WO-2008112178 A1 | 9/2008 |
| WO | WO-2009020764 A1 | 2/2009 |
| WO | WO-2009134475 A1 | 11/2009 |
| WO | WO-2010062600 A1 | 6/2010 |
| WO | WO-2010062622 A2 | 6/2010 |
| WO | WO-2011079866 A1 | 7/2011 |
| WO | WO-2011112773 A2 | 9/2011 |
| WO | WO-2012057916 A1 | 5/2012 |
| WO | WO-2012091747 A1 | 7/2012 |
| WO | WO-2013016268 A1 | 1/2013 |
| WO | WO-2013019853 A1 | 2/2013 |
| WO | WO-2013036630 A1 | 3/2013 |
| WO | WO-2013096260 A1 | 6/2013 |
| WO | WO-2013138786 A1 | 9/2013 |
| WO | WO-2013155117 A1 | 10/2013 |
| WO | WO-2014099423 A1 | 6/2014 |
| WO | WO-2015059570 A1 | 4/2015 |
| WO | WO-2015187426 A1 | 12/2015 |
| WO | WO-2017044904 A1 | 3/2017 |
| WO | WO-2017062508 A1 | 4/2017 |
| WO | WO-2018007914 A1 | 1/2018 |

OTHER PUBLICATIONS

U.S. Appl. No. 13/045,421 / U.S. Pat. No. 9,248,278, filed Mar. 10, 2011 / Feb. 2, 2016.

U.S. Appl. No. 13/045,435 / U.S. Pat. No. 10,925,637, filed Mar. 10, 2011 / Feb. 3, 2021.

U.S. Appl. No. 13/564,584 / U.S. Pat. No. 9,079,019, filed Aug. 1, 2012 / Jul. 14, 2015.

U.S. Appl. No. 13/718,806 / U.S. Pat. No. 9,108,053, filed Dec. 18, 2012 / Aug. 18, 2015.

U.S. Appl. No. 13/797,100 / U.S. Pat. No. 9,999,763, filed Mar. 12, 2013 / Jun. 19, 2018.

U.S. Appl. No. 13/858,809 / U.S. Pat. No. 8,606,358, filed Apr. 8, 2013 / Dec. 10, 2013.

U.S. Appl. No. 14/061,614 / U.S. Pat. No. 9,072,897, filed Oct. 23, 2013 / Jul. 7, 2015.

U.S. Appl. No. 14/295,153 / U.S. Pat. No. 9,186,501, filed Jun. 3, 2014 / Nov. 17, 2015.

U.S. Appl. No. 14/453,423 / U.S. Pat. No. 10,195,419, filed Aug. 6, 2014 / Feb. 5, 2019.

U.S. Appl. No. 14/792,430 / U.S. Pat. No. 9,474,906, filed Jul. 6, 2015 / Oct. 25, 2016.

U.S. Appl. No. 14/849,478 / U.S. Pat. No. 9,861,811, filed Sep. 9, 2015 / Jan. 9, 2018.

U.S. Appl. No. 14/882,087 / U.S. Pat. No. 10,471,268, filed Oct. 13, 2015 / Nov. 12, 2019.

U.S. Appl. No. 14/939,955 / U.S. Pat. No. 9,981,122, filed Nov. 12, 2015 / May 29, 2018.

U.S. Appl. No. 15/202,435 / U.S. Pat. No. 9,950,159, filed Jul. 5, 2016 / Apr. 24, 2018.

U.S. Appl. No. 15/202,485 / U.S. Pat. No. 10,327,810, filed Jul. 5, 2016 / Jun. 25, 2019.

U.S. Appl. No. 15/299,399 / U.S. Pat. No. 10,016,603, filed Oct. 20, 2016 / Jul. 10, 2018.

U.S. Appl. No. 15/853,543 / U.S. Pat. No. 10,661,078, filed Dec. 22, 2017 / May 26, 2020.

U.S. Appl. No. 15/944,730 / U.S. Pat. No. 10,828,490, filed Apr. 3, 2018 / Nov. 10, 2020.

U.S. Appl. No. 15/948,945 / U.S. Pat. No. 10,449,355, filed Apr. 9, 2018 / Oct. 22, 2019.

(56)                References Cited

OTHER PUBLICATIONS

U.S. Appl. No. 16/264,632 / U.S. Pat. No. 11,103,706, filed Jan. 31, 2019 / Aug. 31, 2021.
U.S. Appl. No. 16/443,819 / U.S. Pat. No. 11,406,421, filed Jun. 17, 2019 / Aug. 9, 2022.
U.S. Appl. No. 16/656,500 / U.S. Pat. No. 11,376,427, filed Oct. 17, 2019 / Jul. 5, 2022.
U.S. Appl. No. 16/817,574 / U.S. Pat. No. 10,926,083, filed Mar. 12, 2020 / Feb. 23, 2021.
U.S. Appl. No. 17/092,073, filed Nov. 6, 2020.
U.S. Appl. No. 17/173,121, filed Feb. 10, 2021.
U.S. Appl. No. 17/411,713 / U.S. Pat. No. 11,331,488, filed Aug. 25, 2021 / May 17, 2022.
U.S. Appl. No. 17/647,341 / U.S. Pat. No. 11,471,670, filed Jan. 6, 2022 / Oct. 18, 2022.
U.S. Appl. No. 17/660,375, filed Apr. 22, 2022.
U.S. Appl. No. 17/810,586, filed Jul. 1, 2022.
U.S. Appl. No. 17/812,981, filed Jul. 15, 2022.
U.S. Appl. No. 17/812,989, filed Jul. 15, 2022.
U.S. Appl. No. 17/816,519, filed Aug. 1, 2022.
U.S. Appl. No. 18/046,835, filed Oct. 14, 2022.
Airaksinen, et al., Chapter 4. European guidelines for the management of chronic nonspecific low back pain, European spine journal [I: official publication of the European Spine Society, the European Spinal Deformity Society, and the European Section of the Cervical Spine Research Society 15 Suppl 2:S192-300 (2006), http://www.ncbi.nlm.nih.gov/pubmed/16550448.
Baker, et al., Clinical Uses of Neuromuscular Electrical Stimulation, NeuroMuscular Electrical Stimulation—A Practical Guide, 4th ed., Rancho Los Amigos Research and Education Institute Inc (pp. 47-66) (2000).
Bhadra, et al., Peripheral nerve stimulation for restoration of motor function, Journal of Clinical Neurophysiology: Official Publication of the American Electroencephalographic Society, 14(5):378-33 (Sep. 1997).
Bogie, et al., Effects of Regular Use of Neuromuscular Electrical Stimulation on Tissue Health, Journal of Rehabilitation Research and Development, 40(6):469-475 (2003) available at: http://www.ncbi.nlm.nih.gov/pubmed/15077659 (Accessed Jan. 18, 2011).
Bowman, et al., Effects of Waveform Parameters on Comfort during Transcutaneous Neuromuscular Electrical Stimulation, Annals of Biomedical Engineering, 13:59-74 (1985).
Bradford, et al., Surface Electrical Stimulation in the Treatment of Idiopathic Scoliosis: Preliminary Results in 30 Patients, Spine, 8(7):757-764 (1983).
Brazier, et al., A Comparison of the EQ-5D and SF-6D Across Seven Patient Groups, Health Economics, 13:873-884 (2004).
Chou et al., "Interventional Therapies, Surgery, and Interdisciplinary Rehabilitation for Low Back Pain: An Evidence-Based Clinical Practice Guideline From the American Pain Society." Spine, 34(10):1066-1077 (2009).
Coghlan, et al., Electrical Muscle Stimulation for Deep Stabilizing Muscles in Abdominal Wall, Conference proceedings: Annual International Conference of the IEEE Engineering in Medicine and Biology Society, IEEE Engineering in Medicine and Biology Society, Conference, 2008 (pp. 2756-2759)available at: http://www.ncbi.nlm.nih.gov/pubmed/19163276.
Coghlan, et al., Neuromuscular Electrical Stimulation Training Results in Enhanced Activation of Spinal Stabilizing Muscles During Spinal Loading and Improvements in Pain Ratings, Conference proceedings: Annual International Conference of the IEEE Engineering in Medicine and Biology Society, IEEE Engineering in Medicine and Biology Society, Conference, 2011 (pp. 7622-7625) available at: http://www.ncbi.nlm.nih.gov/pubmed/22256103.
Costa et al., Motor Control Exercise for Chronic Low Back Pain: A Randomized Placebo-Controlled Trial, Physical Therapy, 89(12):1275-1286 (2009).
Crago, et al., The Choice of Pulse Duration for Chronic Electrical Stimulation Via Surface, Nerve, and Intramuscular Electrodes, Annals of Biomedical Engineering, 2(3):252-264 (1974).

CRITERION Inc., NMES Treatment Protocols, 3 pages (accessed Jun. 7, 2012) available at http://www.criterionmed.com/PDF/NMES%20Treatment%20Protocols.pdf.
Deckers, et al., Chronic Low Back Pain: Restoration of Dynamic Stability, Neuromodulation, 18:478-486 (2015).
Durham, et al., Surface Electrical Stimulation Versus Brace in Treatment of Idiopathic Scoliosis, Spine, 15(9):888-891 (1990).
Dworkin et al., Interpreting the Clinical Importance of Treatment Outcomes in Chronic Pain Clinical Trials: IMMPACT Recommendations, The Journal of Pain, 9(2):105-121 (2008).
Eldabe et al., "Complications of Spinal Cord Stimulation and Peripheral Nerve Stimulation Techniques: A Review of the Literature." Pain Medicine, 17:325-336 (2016).
EMPI, Low Back Syndrome/Chronic Low Back Pain, NMES Guidelines for Treatment, 2 pages (2003).
Extended European Search Report dated Jan. 7, 2013 in EP Patent Appl. Serial No. 12176863 (0231).
Extended European Search Report dated Feb. 24, 2020 in EP Patent Appl. Serial No. 08726632.6.
Extended European Search Report dated Mar. 5, 2015 in EP Patent Appl. Serial No. 14189412.1.
Extended European Search Report dated Sep. 30, 2019 in EP Patent Appl. Serial No. 19173003.5.
Farrar et al., "Use of the Cumulative Proportion of Responders Analysis Graph to Present Pain Data Over Range of Cut-Off Points: Making Clinical Trial Data More Understandable." J Pain Symptom Manage, 31(4):369-377 (2006).
Federov et al., "Consequences of dichotomization." Pharmaceut. Statist., 8:50-61 (2009).
Ferreira, et al., Comparison of general exercise, motor control exercise and spinal manipulative therapy for chronic low back pain: A randomized trial, Pain, 131(1-2):31-37 (2007) available at: http://www.ncbi.nlm.nih.gov/pubmed/17250965.
Follett, et al., Prevention and Management of Intrathecal Drug Delivery and Spinal Cord Stimulation System Infections, Anesthesiology, 100:1582-94 (2004).
Freeman, et al., The Role of the Lumbar Multifidus in Chronic Low Back Pain: A Review, American Academy of Physical Medicine and Rehabilitation, 2:142-146 (2010).
Friedman, et al., Electrical stimulation for scoliosis, American Family Physician, 25(4):155-160 (1982) available at: http://www.ncbi.nlm.nih.gov/pubmed/6978055 (Accessed Oct. 19, 2011).
Garmirian , et al., Discriminating Neurogenic from Myopathic Disease via Measurement of Muscle Anisotrophy, Muscle Nerve, 39(1):16-24 (2009) (abstract).
Gazelle, et al., Tumor Ablation with Radio-frequency Energy, Radiology, 217(3):633-646 (2000).
Ghamkhar, et al., *Application of rehabilitative ultrasound in the assessment of low back pain: a literature review*, Journal of Bodywork & Movement Therapies, 15(4):465-477 (2011).
Gilmore, et al., A Review of Peripheral Nerve Stimulation Techniques Targeting the Medial Branches of the Lumbar Dorsal Rami in the Treatment of Chronic Low Back Pain, Pain Medicine, 21(S1):S41-S46 (2020).
Glaser, et al., Electrical Muscle Stimulation as an Adjunct to Exercise Therapy in the Treatment of Nonacute Low Back Pain: A Randomized Trial, The Journal of Pain, 2(5), pp. 295-300 (2001).
Gondin, et al., "Electromyostimulation Training Effects on Neural Drive and Muscle Architecture." Med. Sci. Sports Exerc., 37(8):1291-1299, (2005).
Gondin, et al., Electromyostimulation Training Effects on Neural Drive and Muscle Architecture, Medicine & Science in Sports & Exercise, 37(8):1291-1299 (Aug. 2005).
Gorman, et al., The Effect of Stimulus Parameters on the Recruitment Characteristics of Direct Nerve Stimulation, IEEE Transactions on Bio-medical Engineering, 30 (7): 407-414 (1983).
Haemmerich, et al., Thermal Tumour Ablation: Devices, Clinical Applications and Future Directions, Int. J. Hyperthermia, 21(8):755-760 (2005) (abstract).
Hagg, et al., The Clinical Importance of Changes in Outcome Scores After Treatment for Chronic Low Back Pain, Eur. Spine. J., 12:12-20 (2003).

(56)            References Cited

OTHER PUBLICATIONS

Hauggaard et al., "Specific spinal stabilisation exercises in patients with low back pain—a systematic review." Physical Therapy Reviews, 12(3):233-248 (2007).

Hayek et al., "Treatment-Limiting Complications of Percutaneous Spinal Cord Stimulator Implants: A Review of Eight Years of Experience from an Academic Center Database." Neuromodulation, 18:603-609 (2015).

Hebert et al., *The Relationship of Transversus Abdominis and Lumbar Multifidus Activation and Prognostic Factors for Clinical Success With a Stabilization Exercise Program: A Cross-Sectional Study,* Arch. Phys. Med. Rehabil., 91:78-85 (2010).

Herbert, et al., Scoliosis Treatment in Children Using a Programmable, Totally Implantable Muscle Stimulator (ESI), IEEE Transactions on Biomedical Engineering, 36(7): 801-802(Jul. 1989).

Hides et al., *Long-Term Effects of Specific Stabilizing Exercises for First-Episode Low Back Pain, Spine,* 26(11): E243-248 (2001).

Hodges, et al., Intervertebral Stiffness of the Spine is Increased by Evoked Contraction of Transversus Abdominis and the Diaphragm: in Vivo Porcine Studies, Spine 28(23):2594-2601 (Dec. 1, 2003) (abstract).

Hodges., Is there a Role for Transversus Abdominis in Lumbo-Pelvis Stability?, Manual Therapy, 4(2):74-86, (1999).

Holm, et al., Sensorimotor Control of the Spine, J. Electromyogr. Kinesiol., 12(3):219-234 (2002), (Abstract).

Hortobagyi, et al., Neural adaptations to Electrical Stimulation Strength Training, European Journal of Applied Physiology, 2011 (pp. 2439-2449) available at: http://www.ncbi.nlm.nih.gov/pubmed/21643920 (Accessed Jul. 19, 2011).

Informal Response to Written Opinion dated Jan. 17, 2012 in Int'l PCT Patent Appl. Serial No. PCT/US2011/027834 (0410).

International Search Report & Written Opinion dated Apr. 5, 2013 in Int'l PCT Patent Application Serial No. PCT/US2012/070259 (0610).

International Search Report & Written Opinion dated Jan. 19, 2016 in Int'l PCT Patent Appl. Serial No. PCT/IB2015/055926 (0910).

International Search Report & Written Opinion dated Jun. 25, 2008 in Int'l PCT Patent Appl. No. PCT/US08/03126 (0210).

International Search Report & Written Opinion dated Oct. 20, 2017 in Int'l PCT Patent Appl. Serial No. PCT/IB2017/053546 (1310).

International Search Report & Written Opinion dated Sep. 28, 2017 in Int'l PCT Patent Appl. Serial No. PCT/IB2017/053945 (1210).

International Search Report & Written Opinion dated Mar. 19, 2015 in Int'l PCT Patent Appl. Serial No. PCT/IB2014/002920 (0810).

International Search Report & Written Opinion dated Sep. 3, 2013 in Int'l PCT Application No. PCT/US2013/045223 (0710).

International Search Report & Written Opinion dated Oct. 17, 2012 in Int'l PCT Patent Appl. No. PCT/US12/49148 (0510).

International Search Report & Written Opinion dated Oct. 19, 2011 in Int'l PCT Patent Appl. No. PCT/US11/27834, 12 pages (0410).

International Search Report and Written Opinion dated Jan. 26, 2016 in Int'l PCT Patent Appl. Serial No. PCT/IB2015/057838 (1010).

International Search Report and Written Opinion dated Oct. 16, 2015 in Int'l PCT Patent Appl. Serial No. PCT/US2015/032732 (1110).

Jinkins, Randy, The Anatomic and Physiologic Basis of Local, Referred and Radiating Lumbosacral Pain Syndromes Related to Disease of the Spine, J. Neuroradiol., 31:163-80 (2004).

Keller, et al., Muscular Contributions to Dynamic Dorsoventral Lumbar Spine Stiffness, Eur. Spine J. 16(2): 245-254 (Apr. 29, 2006).

Kiesel, et al., Measurement of Lumbar Multifidus Muscle Contraction with Rehabilitative Ultrasound Imaging, Manual Therapy, 12(2):161-166 (2007) available at: http://www.ncbi.nlm.nih.gov/pubmed/16973400.

Lauridsen, et al., Responsiveness and Minimal Clinically Important Difference for Pain and Disability Instruments in Low Back Pain Patients, BMC Musculoskeletal Disorders, 7(82):16 pages (2006).

Lieber, Richard., Comparison between Animal and Human Studies of Skeletal Muscle Adaptation to Chronic Stimulation, Clinical Orthopaedics and Related Research, 233:19-24 (1988).

Lieber, Richard L., Skeletal Muscle Adaptability. II: Muscle Properties Following Spinal-Cord Injury, Developmental Medicine and Child Neurology, 28(4):533-542 (Aug. 1986).

Lieber, Richard L., Skeletal Muscle Adaptability. III: Muscle Properties Following Chronic Electrical Stimulation, Developmental medicine and child neurology, 28(5):662-670 (Oct. 1986).

Mcintosh, et al., Low back pain (chronic), Clin. Evid., 10:1-28(2008).

Medtronic Extension Passer 3555 Accessory Kit—Technical Instructions, 2 pages (2001).

Medtronic Interstim Therapy 3093 & 3889—Implant Manual, 38 pages (2010).

Medtronic, Kinetra, Soletra, and Itrel II, 8870, Neurostimulators for Deep Brain Stimulation (DBS), Software Application Card, Programming Guide for Software A, Dec. 1, 2003, Published 2005, Retrieved from the Internet: URL: http://www.boala-parkinson.ro/Carti%20tehnice/dbs-prog8870-gd.pdf [retrieved Aug. 23, 2018].

Medtronic Model 3464 Receiver/Extension Internalization Manual, SE-4 for Spinal Cord Stimulation (SCS), 7 pages (1986).

MicroProbes for Life Science, Nerve Cuff electrodes,2018, available at https://microprobes.com/products/peripheral-electrodes/nerve-cuff, accessed Mar. 5, 2018.

Miyatani, et al., Validity of Estimating Limb Muscle Volume by Bioelectrical Impedance, J. Appl. Physiol., 91:386-394, (2001).

Mortimer, et al., Intramuscular electrical stimulation: tissue damage, Annals of Biomedical Engineering, 8(3):235-244 (1980).

Mortimer, et al., Peripheral Nerve and Muscle Stimulation. In: Horch KW, Dhillon G, eds, Neuroprosthetics: Theory and Practice (Series on Bioengineering & Biomedical Engineering—vol. (2), 2005, World Scientific Publishing Company, (pp. 1-48).

Nachemson, et al., Effectiveness of Treatment with a Brace in Girls Who Have Adolescent Idiopathic Scoliosis, The Journal of Bone and Joint Surgery, 77-A(6):815-822 (Jun. 1995).

OAAO Bock, ActiGait Implantable Drop Foot Stimulator, Surgeon Manual, 2006 (28 pages).

O'Donnell, et al., Electrical Stimulation in the Treatment of Idiopathic Scoliosis, Clinical Orthopaedics and Related Research, No. 229:107-112 (Apr. 1988).

Ostelo et al., Interpreting Change Scores for Pain and Functional Status in Low Back Pain: Towards International Consensus Regarding Minimal Important Change, Spine, 33(1):90-94 (2008).

Paicius, et al., Peripheral Nerve Field Stimulation for the Treatment of Chronic Low Back Pain: Preliminary Results of Long-Term Follow-up: A Case Series, Neuromodulation, 10(3):279-290 (2007) available at: http://www.blackwell-synergy.com/doi/abs/10.llll/j.1525-1403.2007.00116.x-.

Panjabi, Manohar., A hypothesis of Chronic Back Pain: Ligament Sub-Failure Injuries Lead to Muscle Control Dysfunction, European spine journal: official publication of the European Spine Society, the European Spinal Deformity Society, and the European Section of the Cervical Spine Research Society 15(5): 668-676, (May 2006), http://www.ncbi.nlm.nih.gov/pubmed/16047209.

Panjabi, Manohar., The Stabilizing System of the Spine, Part 1, Function, Dysfunction, Adaptation, and Enhancement, Journal of Spinal Disorders, 5(4)383-389 (Dec. 1992), Discussion 397., http://www.ncbi.nlm.nih.gov/pubmed/1490034.

Panjabi, Manohar., The stabilizing system of the spine, Part II, Neutral zone and instability hypothesis, Journal of Spinal Disorders, 5(4):390-396 (Dec. 1992), Discussion 397. http://www.ncbi.nlm.nih.gov/pubmed/1490035.

PCT Written Opinion dated Aug. 23, 2013 in Int'l PCT Patent Appl. Serial No. PCT/US2010/049148 (0510).

Peckham, et al., Functional Electrical Stimulation for Neuromuscular Applications, Annual review of Biomedical Engineering, 7:327-360 (2005) available at: http://www.ncbi.nlm.nih.gov/pubmed/16004574.

Peterson, et al., Long-term Intramuscular Electrical Activation of the Phrenic Nerve: Safety and Reliability, IEEE Transactions on Bio-medical Engineering, 41(12):1115-1126 (1994).

(56)                  References Cited

OTHER PUBLICATIONS

Poitras, et al., Evidence-informed Management of Chronic Low Back Pain with Transcutaneous Electrical Nerve Stimulation, Interferential Current, Electrical Muscle Stimulation, Ultrasound, And Thermotherapy, The Spine Journal, 8:226-233 (2008).

Reed B., The Physiology of Neuromuscular Electrical Stimulation, Pediatric Physical Therapy, 9(3):96-102 (1997) available at: http://journals.lww.com/pedpt/pages/articleviewer.aspx?year=1997&issue=00-930&article=00002&type=abstract.

Rosatelli, et al., Three-Dimensional Study of the Musculotendinous Architecture Of Lumber Multifidus and its Functional Implications, Clinical Anatomy, 21(6):539-544 (Sep. 2008).

RS Medical, RS-4M Muscle Stimulator, available at http://www.rsmedical.com/documents/fact_sheet_RS4m.pdf (last visited Jul. 19, 2012).

Russo, et al., Muscle Control and Non-specific Chronic Low Back Pain, Neuromodulation: Technology at the Neural Interface, 21:1-9 (2017).

Rutkove., Electrical Impedance Myography: Background, Current State, and Future Directions, Muscle Nerve, 40(6):936-946 (2009).

Schwartz, et al., Therapeutic Electrical Stimulation of the Hypoglossal Nerve in Obstructive Sleep Apnea, Arch Otolaryngal Head Neck Surg., 127:1216-1223 (2001).

Senn et al., "Measurement in clinical trials: A neglected issue for statisticians?" Statist. Med., 28:3189-3209 (2009).

Sheffler et al., Neuromuscular Electrical Stimulation in Neurorehabilitation, Muscle Nerve, 35:562-590 (2007).

Sluijter, Radiofrequency Ablation in the Management of Spinal Pain, C212, IV(1):10-15, (2006).

Soer et al., *Clinimetric properties of the EuroQol-50 in patients with chronic low backpain,* The Spine Journal, 12:1035-1039 (2012).

Stokes, et al., Surface EMG Electrodes Do Not Accurately Record from Lumbar Multifidus Muscles, Clin. Biomech, 18(1):9-13, (2003), (Abstract Only).

Unit III—The Spine, "Motions of the Spine," available at https://courses.vcu.edu/DANC291-003/unit_3.htm, accessed Mar. 5, 2018.

Van Buyten et al., *Neuromuscular Reactivation—A New Therapy for Patients with Chronic Low Back Pain (CLBP): Results of a European Multicenter Feasibility Study,* Neuromodulation, 16:e176 (2013).

Van, et al., The Use of Real-Time Ultrasound Imaging for Biofeedback of Lumbar Multifidus Muscle Contraction in Healthy Subjects, The Journal of Orthopaedic and Sports Physical Therapy, 36(12):920-925 (2006) available at: http://www.ncbi.n1m.nih.gov/pubmed/17193869.

Verrills, et al., Peripheral Nerve Stimulation: A Treatment for Chronic Low Back Pain and Failed Back Surgery Syndrome?, Neuromodulation: Technology at the Neural Interface, 12(1):68-75, (2009).

Vrbova et al., Application of Muscle/Nerve Stimulation in Health and Disease, Springer Verlag (2008) available at: http://books.google.com/books?h1=en&1r=&id=jb8fDGxkbqEC&oi=fn-d&pg=PA1&dq=Application+of+Muscle/Nerve+Stimulation+in+Health+and+-Disease&ots=CMV5rXiDQD&sig=Wg8ulYOC4PgvVDzcjdwBub5U2To (Accessed Jun. 2, 2011).

Wallwork, et al., The Effect of Chronic Low Back Pain on Size and Contraction of the Lumbar Multifidus Muscle, Manual Therapy, 14(5):496-500 (2009) available at: http://www.ncbi.nlm.nih.gov/pubmed/19027343.

Ward, et al., Architectural Analysis and Intraoperative Measurements Demonstrate the Unique Design of the Multifidus for Lumbar Spine Stability, J. Bone Joint Surg. [Am.] 91:176-185, PMC2663324 (2009).

Wikipedia., Blunt Dissection, Updated Feb. 14, 2018, available at https://en.wikipedia.org/wiki/Blunt_dissection.

Wikipedia, Dorsal Ramus of Spinal Nerve, Updated Feb. 12, 2018, available at https://en.wikipedia.org/wiki/Dorsal_ramus_of_spinal_nerve.

Wikipedia, "Interference Fit," http://en.wikipedia.org/wiki/Interference. sub.--fit, accessed Dec. 4, 2014.

Wikipedia, Time-division Multiplexing, https://en.wikipedia.org/wiki/Time-division.sub.--multiplexing (accessed Nov. 12, 2015).

Wikipedia, Ventral Ramus of Spinal Nerve, Updated Feb. 12, 2018, available at https://en.wikipedia.org/wiki/Ventral_ramus_of spinal_nerve.

Wright et al., Morphologic and Histochemical Characteristics of Skeletal Muscle after Long- Term Intramuscular Electrical Stimulation, Spine, 17(7):767-770 (1992) available at: http://www.ncbi.nlm.nih.gov/pubmed/1502640 (Accessed Aug. 2, 2011).

Written Opinion of the International Preliminary Examining Authority dated Feb. 3, 2014 in Int'l PCT Patent Appl. Serial No. PCT/US2012/070259 (0610).

Zundert, et al., Radiofrequency Treatment for Chronic Pain Syndromes, CPD Anaesthesia, 6(1):13-17 (2004).

"Ineffective treatments for low back pain might actually make the pain (and treatment worse)," The Mighty, Military News, https://www.wearethemight.com/sponsored-content/ineffective-treatments-for-low-back-pain-might-actually-make-the-pain-and-treatment-worse/, accessed Oct. 10, 2023.

Jensen, et al., Mechanisms of spinal cord stimulation for the treatment of pain: Still in the dark after 50 years, Eur. J. Pain, 23:652-659 (2019).

"Mainstay Medical Announces Positive Outcomes From Landmark RESTORE Clinical Trial of ReActiv8 (R)," Businesswire.com (Jan. 15, 2025).

Schwab, et al., Restorative Neurostimulation Therapy Compared to Optimal Medical Management: A Randomized Evaluation (RESTORE) for the Treatment of Chronic Mechanical Low Back Pain due to Multifidus Dysfunction, Pain. Ther. 24:401-423 (2025).

* cited by examiner

SYSTEMS AND METHODS FOR EXTRACTING AN ELECTRODE LEAD

CROSS-REFERENCE TO RELATED APPLICATIONS

This application claims priority to U.S. Provisional Patent Application Ser. No. 63/269,756, filed Mar. 22, 2023, the entire contents of which are incorporated herein by reference.

FIELD OF USE

The present disclosure is directed to a lead extraction system and methods for extracting an electrode lead implanted within a patient.

BACKGROUND

The human back is a complicated structure including bones, muscles, ligaments, tendons, nerves and other structures. The spinal column has interleaved vertebral bodies and intervertebral discs, and permits motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Back pain in the lower or lumbar region of the back is common. In many cases, the cause of back pain is unknown. It is believed that some cases of back pain are caused by abnormal mechanics of the spinal column. Degenerative changes, injury of the ligaments, acute trauma, or repetitive microtrauma may lead to back pain via inflammation, biochemical and nutritional changes, immunological factors, changes in the structure or material of the endplates or discs, and pathology of neural structures.

The spinal stabilization system may be conceptualized to include three subsystems: 1) the spinal column, which provides intrinsic mechanical stability; 2) the spinal muscles, which surround the spinal column and provide dynamic stability; and 3) the neuromotor control unit, which evaluates and determines requirements for stability via a coordinated muscle response. In patients with a functional stabilization system, these three subsystems work together to provide mechanical stability. It is applicant's realization that low back pain results from dysfunction of these subsystems.

The spinal column consists of vertebrae and ligaments, e.g. spinal ligaments, disc annulus, and facet capsules. There has been an abundance of in-vitro work in explanted cadaver spines and models evaluating the relative contribution of various spinal column structures to stability, and how compromise of a specific column structure will lead to changes in the range of motion of spinal motion segments.

The spinal column also has a transducer function, to generate signals describing spinal posture, motions, and loads via mechanoreceptors present in the ligaments, facet capsules, disc annulus, and other connective tissues. These mechanoreceptors provide information to the neuromuscular control unit, which generates muscle response patterns to activate and coordinate the spinal muscles to provide muscle mechanical stability. Ligament injury, fatigue, and viscoelastic creep may corrupt signal transduction. If spinal column structure is compromised, due to injury, degeneration, or viscoelastic creep, then muscular stability must be increased to compensate and maintain stability.

Muscles provide mechanical stability to the spinal column. This is apparent by viewing cross section images of the spine, as the total area of the cross sections of the muscles surrounding the spinal column is larger than the spinal column itself. Additionally, the muscles have much larger lever arms than those of the intervertebral disc and ligaments.

Under normal circumstances, the mechanoreceptors exchange signals with the neuromuscular control unit for interpretation and action. The neuromuscular control unit produces a muscle response pattern based upon several factors, including the need for spinal stability, postural control, balance, and stress reduction on various spinal components.

It is believed that in some patients with back pain, the spinal stabilization system is dysfunctional. With soft tissue injury, mechanoreceptors may produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Conversely, muscles can disrupt the spinal stabilization system by going into spasm, contracting when they should remain inactive, or contracting out of sequence with other muscles. As muscles participate in the feedback loop via mechanoreceptors in the form of muscle spindles and golgi tendon organs, muscle dysfunction may further compromise normal muscle activation patterns via the feedback loops.

Trunk muscles may be categorized into local and global muscles. The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, with its vertebra-to-vertebra attachments is an example of a muscle of the local system. Another example is the transverse abduminus, with its direct attachments to the lumbar vertebrae through the thoracolumbar fascia. The thoracolumbar fascia is a deep investing membrane which covers the deep muscles of the back of the trunk. The thoracolumbar fascia includes superficial fascia and deep fascia. The superficial fascia is traditionally regarded as a layer of areolar connective or adipose tissue immediately beneath the skin, whereas deep fascia is a tougher, dense connective tissue continuous with it. Deep fascia is commonly arranged as sheets and typically forms a stocking around the muscles and tendons beneath it. Superficial fascia fibers run in the transverse direction, whereas deep fascia fibers run in a cranial-caudal direction.

The multifidus is the largest and most medial of the lumbar back muscles. It has a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles that attach to the mamillary processes attach to the capsules of the facet joints next to the mamillary processes. The fascicles arriving from the spinous process of a given vertebra are innervated by the medial branch of the dorsal ramus that issues from below that vertebra. The dorsal ramus is part of spinal nerve roots formed by the union of dorsal root fibers distal to the dorsal root ganglion and ventral root fibers. The dorsal root ganglion is a collection of sensory neurons that relay sensory information from the body to the central nervous system.

The global muscle system encompasses the large, superficial muscles of the trunk that cross multiple motion segments, and do not have direct attachment to the vertebrae. These muscles are the torque generators for spinal motion, and control spinal orientation, balance the external loads applied to the trunk, and transfer load from the thorax to the pelvis. Global muscles include the oblique internus abdominus, the obliquus externus abdmonimus, the rectus abdominus, the lateral fibers of the quadratus lumborum, and portions of the erector spinae.

Normally, load transmission is painless. Over time, dysfunction of the spinal stabilization system is believed to lead to instability, resulting in overloading of structures when the spine moves beyond its neutral zone. The neutral zone is a range of intervertebral motion, measured from a neutral position, within which the spinal motion is produced with a minimal internal resistance. High loads can lead to inflammation, disc degeneration, facet joint degeneration, and muscle fatigue. Since the endplates and annulus have a rich nerve supply, it is believed that abnormally high loads may be a cause of pain. Load transmission to the facets also may change with degenerative disc disease, leading to facet arthritis and facet pain.

Functional electrical stimulation (FES) is the application of electrical stimulation to cause muscle contraction to re-animate limbs following damage to the nervous system such as with stroke or spine injury. FES has been the subject of much prior art and scientific publications. In FES, the goal generally is to bypass the damaged nervous system and provide electrical stimulation to nerves or muscles directly which simulates the action of the nervous system. One lofty goal of FES is to enable paralyzed people to walk again, and that requires the coordinated action of several muscles activating several joints. The challenges of FES relate to graduation of force generated by the stimulated muscles, and the control system for each muscle as well as the system as a whole to produce the desired action such as standing and walking.

With normal physiology, sensors in the muscle, ligaments, tendons and other anatomical structures provide information such as the force a muscle is exerting or the position of a joint, and that information may be used in the normal physiological control system for limb position and muscle force. This sense is referred to as proprioception. In patients with spinal cord injury, the sensory nervous system is usually damaged as well as the motor system, and thus the afflicted person loses proprioception of what the muscle and limbs are doing. Functional electrical stimulation (FES) systems often seek to reproduce or simulate the damaged proprioceptive system with other sensors attached to a joint or muscle. FES has also been used to treat spasticity, characterized by continuous increased muscle tone, involuntary muscle contractions, and altered spinal reflexes which leads to muscle tightness, awkward movements, and is often accompanied by muscle weakness. Spasticity results from many causes including cerebral palsy, spinal cord injury, trauma, and neurodegenerative diseases.

Neuromuscular Electrical Stimulation (NMES) is a subset of the general field of electrical stimulation for muscle contraction, as it is generally applied to nerves and muscles which are anatomically intact, but malfunctioning in a different way. NMES may be delivered via an external system or, in some applications, via an implanted system. NMES via externally applied skin electrodes has been used to rehabilitate skeletal muscles after injury or surgery in the associated joint. This approach is commonly used to aid in the rehabilitation of the quadriceps muscle of the leg after knee surgery. Electrical stimulation is known to not only improve the strength and endurance of the muscle, but also to restore malfunctioning motor control to a muscle. See, e.g., Gondin et al., "Electromyostimulation Training Effects on Neural Drive and Muscle Architecture", Medicine & Science in Sports & Exercise 37, No. 8, pp. 1291-99 (August 2005).

The goals and challenges of rehabilitation of anatomically intact (i.e., non-pathological) neuromuscular systems are fundamentally different from the goals and challenges of FES for treating spinal injury patients or people suffering from spasticity. In muscle rehabilitation, the primary goal is to restore normal functioning of the anatomically intact neuromuscular system, whereas in spinal injury and spasticity, the primary goal is to simulate normal activity of a pathologically damaged neuromuscular system.

U.S. Pat. Nos. 8,428,728 and 8,606,358 to Sachs, both assigned to the assignee of the present disclosure, and both incorporated herein in their entireties by reference, describe implanted electrical stimulation devices that are designed to restore neural drive and rehabilitate the multifidus muscle to improve stability of the spine. Rather than masking pain signals while the patient's spinal stability potentially undergoes further deterioration, the stimulator systems described in those applications are designed to reactivate the motor control system and/or strengthen the muscles that stabilize the spinal column, which in turn is expected to reduce persistent or recurrent pain.

While the stimulator systems described in the Sachs patents seek to rehabilitate the multifidus and restore neural drive, use of those systems necessitates the implantation of one or more electrode leads in the vicinity of a predetermined anatomical site, such as the medial branch of the dorsal ramus of the spinal nerve to elicit contraction of the lumbar multifidus muscle.

As discussed above, the deep back muscles are covered by the thoracolumbar fascia which comprises superficial fascia running in the transverse direction and deep fascia running in a cranial-caudal direction. There is a risk that electrode lead conductors may experience a tight bend near the location where the lead enters the thoracolumbar fascia when the lead is inserted within the body near the lateral edge of the spine. Such a tight bend may lead to dislodgement of the electrode lead and/or fracture, thereby preventing proper therapy delivery. The difference in directions of the superficial and deep fascia near the insertion site at the lateral edge of the spine may increase the risk of a high stress location on the lead, as described in U.S. Pat. No. 10,327,810 to Shiroff, assigned to the assignee of the present disclosure, and incorporated herein in its entirety by reference. Moreover, the muscles of the lower back are highly mobile and create an environment that can impose large mechanical stresses on electrode leads, resulting in a high risk of lead dislodgement and/or lead fracture. As a result, fracture-inducing shear forces as well as axial forces imposed on a conventional lead by the relative movement of the muscles overlying the back muscles targeted for stimulation may cause the lead to dislodge and/or fracture.

U.S. Pat. No. 9,999,763 to Shiroff, U.S. Pat. No. 9,950,159 to Beck, and 11,103,706 to Sachs, all assigned to the assignee of the present disclosure, and all incorporated herein in their entireties by reference, describe electrode leads having opposite-angled fixation elements, e.g., tines, for sandwiching an anchor site therebetween to anchor the electrodes of the electrode lead in or adjacent to tissue associated with one or more spine stabilizing muscles associated with local segmental control of a lumbar spine within a back of a patient. In addition, as the electrode leads may be implanted within the patient for a long period of time, tissue ingrowth may grow along the fixation elements, thereby adding further anchoring support to the electrode lead. However, there may be circumstances in which the electrode lead may need to be removed from the patient's body and/or replaced with another electrode lead. As the fixation elements may be embedded in tissue, simply retracting the electrode lead by applying a pulling force may fracture the lead elements, requiring a more invasive and time-consuming procedure for removal thereof.

Accordingly, there exists a need for a lead extraction tool that may safely remove an implanted electrode having fixation elements for anchoring the electrode lead at an anchor site.

SUMMARY

The present disclosure overcomes the drawbacks of previously-known systems and methods by providing a lead extraction system for extracting an implanted electrode lead comprising a fixation element, e.g., proximal and distal fixation elements. The system may include a dilator having a lumen sized and shaped to receive a proximal end of the electrode lead therethrough such that the dilator is slideable along the electrode lead, wherein a distal portion of the dilator may be advanced distally to separate tissue surrounding the electrode lead. Moreover, the dilator may be advanced distally to collapse proximal fixation elements of the fixation element within the lumen of the dilator. The system further may include a trephine having a lumen sized and shaped to receive a proximal end of the dilator therethrough, wherein a distal portion of the trephine has a cutting edge that may be advanced distally to cut tissue surrounding the fixation element to thereby dislodge the implanted electrode lead. For example, the cutting edge of the trephine may be advanced distally to cut tissue surrounding distal fixation elements of the fixation element to thereby dislodge the electrode lead.

The system further may include a sheath having a lumen sized and shaped to receive a proximal end of the electrode lead therethrough such that the sheath is slideable along the electrode lead. A distal portion of the sheath may be advanced distally until it abuts a collar on the electrode lead that is coupled to the proximal fixation elements, thereby preventing further distal advancement of the sheath relative to the electrode lead. Accordingly, the lumen of the dilator may be sized and shaped to receive a proximal end of the sheath therethrough such that the dilator is slideable along the sheath. The sheath may have an outer diameter substantially equal to an outer diameter of the collar. The dilator may be rotated as the distal portion of the dilator is advanced distally to collapse the proximal fixation elements within the lumen of the dilator. Moreover, the distal portion of the dilator may be tapered. For example, a cross-sectional area of the distal portion of the dilator may decrease distally toward a distal end of the dilator.

The cutting edge of the distal portion of the trephine may include a plurality of proximally extending concave edges circumferentially disposed along a distal end of the trephine. In addition, the cutting edge of the distal portion of the trephine may be angled to facilitate cutting of the tissue surrounding the fixation element. Moreover, the trephine may be rotated as the cutting edge of the trephine is advanced distally to cut tissue surrounding the fixation element. The cutting edge of the distal portion of the trephine further may cut at least a portion of the fixation element. A proximal portion of the trephine may include a handle for facilitating rotation of the trephine by a user. At least one of the dilator or trephine may be formed of a rigid material, e.g., stainless steel. Moreover, a proximal portion of the dilator may include one or more textured surfaces configured to facilitate gripping of the dilator. In addition, the dilator may include an alignment marker disposed between two of the one or more textured surfaces, such that the alignment marker may facilitate alignment of the cutting edge of trephine and the distal portion of the dilator. For example, the alignment marker may include a groove extending circumferentially along an outer surface of the dilator. Alternatively, the alignment marker may include a smooth section between the two of the one or more textured surfaces. The system further may include an electrode lead having a fixation element, e.g., proximal and distal fixation elements, for anchoring the electrode lead in or adjacent to tissue associated with one or more spine stabilizing muscles associated with local segmental control of a lumbar spine within a back of a patient.

In accordance with another aspect of the present disclosure, a method for extracting an implanted electrode lead having a fixation element, e.g., proximal and distal fixation elements, from a patient's body is provided. The method may include advancing a dilator distally over a proximal end of the implanted electrode lead to thereby separate tissue surrounding the electrode lead. Moreover, advancing the dilator distally may include advancing the dilator distally over proximal fixation elements of the fixation element to thereby collapse the proximal fixation elements within the lumen of the dilator. The method further may include advancing a trephine distally over a proximal end of the dilator, such that a cutting edge at a distal portion of the trephine cuts tissue surrounding the fixation element, e.g., distal fixation elements of the fixation element, to thereby dislodge the implanted electrode lead; and removing the electrode lead from the patient's body. Prior to advancing the dilator distally over the proximal end of the implanted electrode lead, the method may include advancing a sheath distally over a proximal end of the implanted electrode lead until a distal end of the sheath abuts a collar of the proximal fixation elements. Accordingly, advancing the dilator distally over the proximal end of the implanted electrode lead includes advancing the dilator distally over the proximal end of the sheath.

Moreover, advancing the dilator distally over the proximal end of the implanted electrode lead may include rotating the dilator as the dilator is advanced distally. Additionally, advancing the trephine distally may include rotating the trephine as the trephine is advanced distally to cut the tissue surrounding the fixation element. The method further may include cutting at least a portion of the fixation element, e.g., the distal fixation elements, by advancing the trephine distally over the fixation element to facilitate dislodgement of the implanted electrode lead. In addition, the method may include removing the electrode lead and dilator proximally through the lumen of the trephine, and removing the trephine from the patient's body.

DETAILED DESCRIPTION

Figure 1:
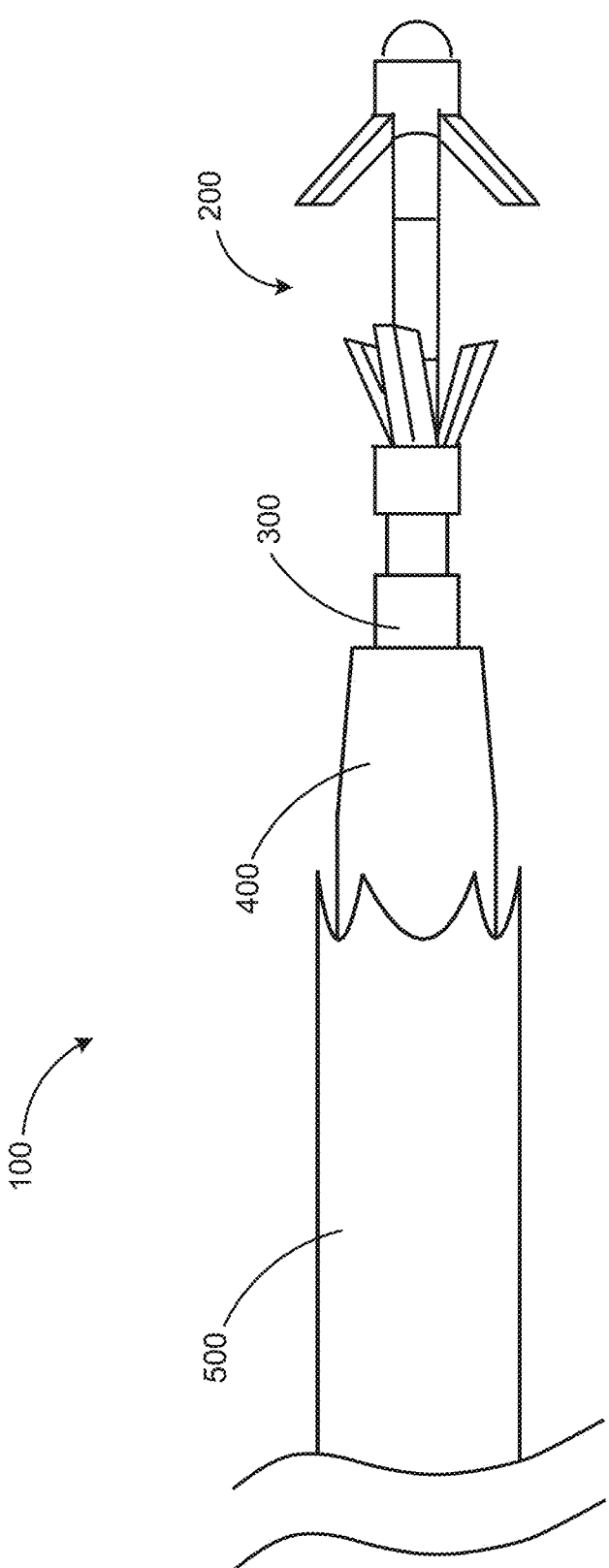
FIG. 1 is a schematic view of an exemplary embodiment of a lead extraction system constructed in accordance with the principles of the present disclosure.

Referring now to FIG. 1, an exemplary lead extraction system is provided. In FIG. 1, components of the system are not depicted to scale on either a relative or absolute basis. As shown in FIG. 1, lead extraction system 100 may include sheath 300, dilator 400, and trephine 500 for extracting implanted electrode lead 200. As described in further detail below, electrode lead 200 may be implanted within a patient's body for providing electrostimulation therapy to treat, e.g., low back pain, by rehabilitating the spine stabilizing muscles associated with local segmental control of a lumbar spine within a back of the patient. As electrode lead 200 remains implanted within the patient, tissue ingrowth may develop along the fixation elements of electrode lead 200, thereby providing further anchoring support to electrode lead 200.

Under circumstances that may necessitate removal of implanted electrode lead 200 from the patient's body, lead extraction system 100 may be used to safely dislodge electrode lead 200 from the surrounding tissue for safe extraction of electrode lead 200 from the patient. For example, upon detachment of the proximal end of electrode lead 200 from a pulse generator, e.g., an implantable pulse generator or an external pulse generator, sheath 300 may be advanced over the proximal end of electrode lead 200 until a distal end of sheath 300 abuts a collar of electrode lead 200 coupled to the proximal fixation elements of electrode lead 200. Dilator 400 then may be advanced over the proximal end of sheath 300 and the proximal fixation elements while simultaneously rotated to thereby collapse the proximal fixation elements toward the lead body of electrode lead 200 within a lumen of dilator 400. Alternatively, sheath 300 may not be required, such that dilator 400 may be advanced directly over the proximal end of electrode lead 200 to collapse the proximal fixation elements of electrode lead 200. Trephine 500 may then be advanced over the proximal end of dilator 400 while simultaneously rotated to thereby cut tissue surrounding the fixation elements of electrode lead 200 and dislodge the distal fixation elements of electrode lead 200. Electrode lead 200, sheath 300, and dilator 400 may then be removed from the patient through the lumen of trephine 500, and trephine 500 may then be removed from the patient to complete the lead extraction process.

Figure 2:
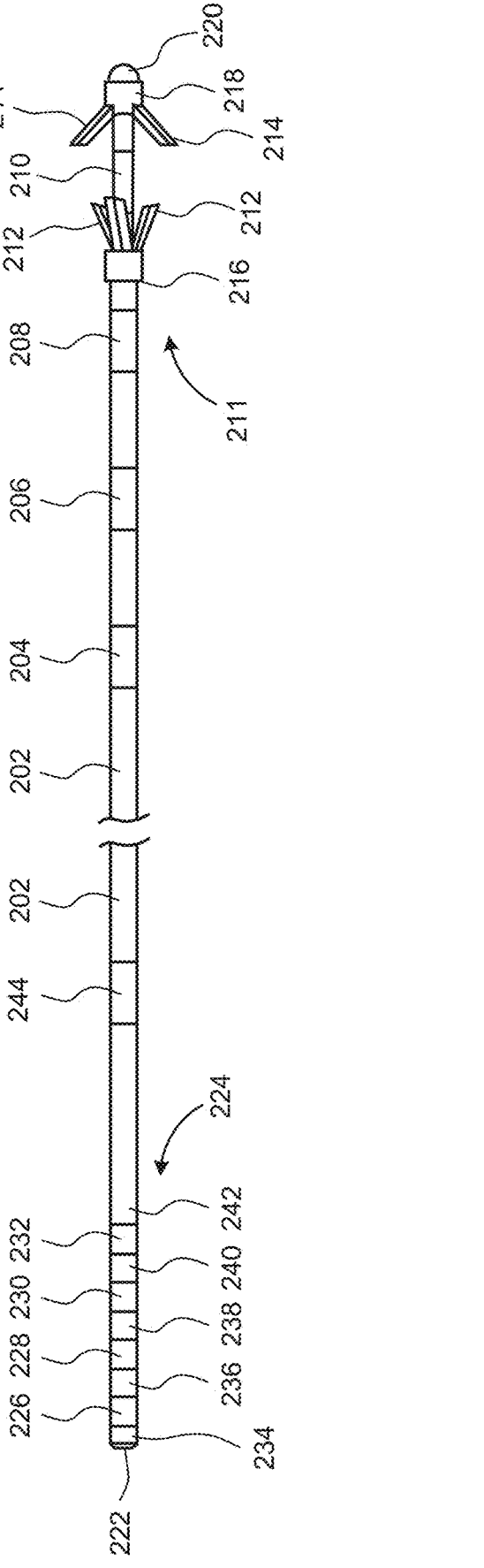
FIG. 2 is a schematic view of an exemplary embodiment of an electrode lead constructed in accordance with the principles of the present disclosure.

Referring now to FIG. 2, an exemplary electrode lead is provided. Electrode lead 200, e.g., an electrostimulation lead, may be coupled to a pulse generator, which may be actuated via an actuator, an external programmer, and a software-based programming system, as described in U.S. Pat. No. 9,950,159 to Beck, the entire contents of which are incorporated herein by reference. As shown in FIG. 2, electrode lead 200 includes lead body 202 having a plurality of electrodes, illustratively, electrodes 204, 206, 208, 210, disposed at distal region 211, the plurality of electrodes electrically coupled to a plurality of contacts, illustratively contacts 226, 228, 230, 232, disposed at proximal region 224, via a plurality of conductors. Electrode lead 200 is configured for implantation in or adjacent to tissue, e.g., nervous tissue, muscle, a ligament, and/or a joint capsule including tissue associated with local segmental control of the lumbar spine.

Lead body 202 is a suitable length for positioning the electrodes in or adjacent to target tissue while the pulse generator is implanted in a suitable location, e.g., the lower back, or alternatively, when the pulse generator is externally worn by the patient. For example, lead body 202 may be between about 30 and 80 cm in length, and preferably about 45 or about 65 cm in length. Lead body 202 is also of a suitable diameter for placement, for example, between about 1 and 2 mm in diameter and preferably about 1.3 mm. Electrodes 204, 206, 208, 210 may be configured to stimulate the tissue at a stimulation frequency and at a level and duration sufficient to cause muscle to contract and may be ring electrodes, partial electrodes, segmented electrodes, nerve cuff electrodes placed around the nerve innervating the target muscle, or the like. Electrodes 204, 206, 208, 210 are a suitable length(s) and spaced apart a suitable distance along lead body 202. For example, electrodes 204, 206, 208, 210 may be about 2-5 mm in length, and preferably about 3 mm, and may be spaced apart about 2-6 mm, and preferably about 4 mm. As will also be understood by one of skill in the art, an electrode lead may contain more or fewer than four electrodes.

As shown in FIG. 2, first and second fixation elements, e.g., proximal fixation elements 212 and distal fixation elements 214 may be coupled to lead body 202 at distal region 211 via first and second fixation rings/collars 216 and 218, respectively. First and second fixation elements 212 and 214 are configured to sandwich an anchor site, e.g., muscle, therebetween to secure electrode lead 200 at a target site without damaging the anchor site. In the illustrated embodiment, proximal fixation elements 212 are positioned between electrode 208 and distal most electrode 210 and distal fixation element 214 is positioned between distal most electrode 210 and end cap 220. The length of and spacing between the fixation elements is defined by the structure around which they are to be placed. In one embodiment, the length of each fixation element is between about 1.5-4 mm and preferably about 2.5 mm and the spacing is between about 2 mm and 10 mm and preferably about 6 mm. Proximal and distal fixation elements 212 and 214 are configured to collapse inward toward lead body 202 in a delivery state and to expand, e.g., due to retraction of a sheath, in a deployed state.

As shown in FIG. 2, proximal fixation elements 212 may be radially offset with respect to distal fixation elements 214. For example, proximal fixation elements 212 may be configured to be radially offset relative to distal fixation elements 214 by prefabricating at least one of first fixation collar 216 and second fixation collar 218 relative to lead body 202 such that at least one of proximal and distal fixation elements 212 and 214 is radially offset with respect to each other. For example, the projections of proximal fixation elements 212 may be radially offset relative to the projections of distal fixation elements 214 by, e.g., approximately 60 degrees. Moreover, proximal and distal fixation elements 212 and 214 may be formed of a flexible material, e.g., a polymer, and may be collapsible and self-expandable when deployed. For example, proximal and distal fixation elements 212 and 214 may collapse inward toward lead body 202 in a delivery state such that they are generally parallel to the longitudinal axis of lead body 202 within a sheath. In the delivery state, the radially offset proximal and distal fixation elements 212 and 214 need not overlap within a sheath.

Further, proximal and distal fixation elements 212 and 214 may expand, e.g., due to retraction of the sheath, in a deployed state. In the deployed state, proximal fixation elements 212 may be angled distally relative to lead body 202, and resist motion in the first direction, e.g., distally, and prevent, in the case illustrated, insertion of the lead too far, as well as migration distally. Distal fixation elements 214 may be angled proximally relative to lead body 202 and penetrate through a tissue plane and deploy on the distal side of the tissue immediately adjacent to the target of stimulation. Distal fixation elements 214 are configured to resist motion in the opposite direction relative to proximal fixation elements 212. This combination prevents migration both proximally and distally, and also in rotation.

While FIG. 2 illustrates proximal and distal fixation elements 212 and 214 on lead body 202, it should be understood that other fixation elements may be used to anchor electrode lead 200 at a suitable location including the fixation elements described in U.S. Pat. No. 9,079,019 to Crosby and U.S. Pat. No. 9,999,763 to Shiroff, both assigned to the assignee of the present disclosure, the entire contents of each of which are incorporated herein by reference.

Lead body 202 further may include stylet lumen 222 extending therethrough. Stylet lumen 222 may be shaped and sized to permit a stylet to be inserted therein, for example, during delivery of electrode lead 200. In one embodiment, end cap 220 is used to prevent the stylet from extending distally out of stylet lumen 222 beyond end cap 220.

As shown in FIG. 2, electrode lead 200 may include contacts 226, 228, 230, 232 at proximal region 224 separated along lead body 202 by a plurality of spacers 234, 236, 238, 240, 242, e.g., insulated tubing. Contacts 226, 228, 230, 232 may comprise an isodiametric terminal and are electrically coupled to electrodes 204, 206, 208, 210, respectively, via, for example, individually coated wires extending between the contacts and electrodes as described in further detail below. A portion of proximal region 224 may be configured to be inserted in the pulse generator. For example, a portion of proximal end 224 may be configured to be inserted in the pulse generator and set-screw retainer 244 may be configured to receive a screw from the pulse generator to secure the portion of electrode lead 200 within the pulse generator.

Figures 3A, 3B:
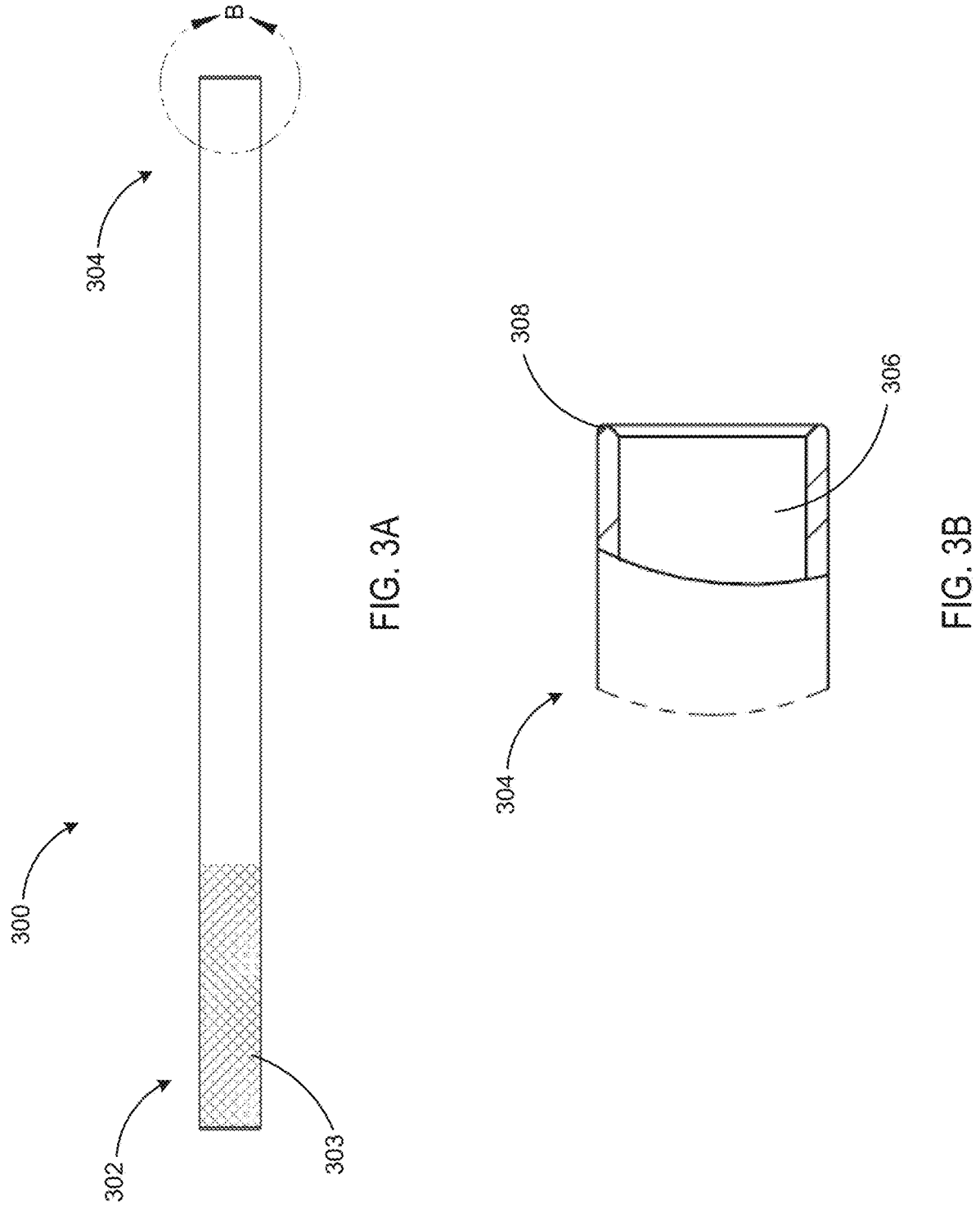
FIG. 3A illustrates an exemplary sheath of the lead extraction system of FIG. 1, constructed in accordance with the principles of the present disclosure.
FIG. 3B is a close-up view of a distal portion of the sheath of FIG. 3A.

Referring now to FIGS. 3A and 3B, an exemplary sheath is provided. As shown in FIG. 3A, sheath 300 includes proximal portion 302 and distal portion 304. As shown in FIG. 3A, at least a portion of proximal region 302 may include textured surface 303 to facilitate gripping by the surgeon during the extraction process, e.g., to advance sheath 300 distally relative to electrode lead 200. For example, textured surface 303 may be debossed into the outer surface of proximal region 302 of sheath 300, e.g., via grit blasting or other machine methods known in the art. Moreover, textured surface 303 need not extend along the entire length of sheath 300. For example, textured surface 303 may extend about 2.5 inches along proximal region 302 of sheath 300. As will be understood by a person having ordinary skill in the art, textured surface 303 may extend along the outer surface of sheath 300 in any manner that permits the surgeon to effectively grip sheath 300 during the lead extraction procedure.

FIG. 3B is a close-up, partial cross-sectional view of distal region 304 of sheath 300, as indicated by circle B. Sheath 300 may be made of a rigid material, e.g., stainless steel, and have lumen 306 extending through an entire length of sheath 300. Lumen 306 is sized and shaped to receive the proximal end of electrode lead 200, such that sheath 300 is slidable over lead body 202 of electrode lead 200. For example, the proximal end of electrode lead 200 may be fed through lumen 306 at distal end 308 of sheath 300, such that sheath 300 may be advanced distally relative to electrode lead 200 until distal end 308 abuts collar 216 coupled to proximal fixation elements 212 of electrode lead 200. As shown in FIG. 1, the outer surface of sheath 300 may have a diameter that is substantially equal to collar 216 of electrode lead 200.

Referring again to FIG. 3B, distal end 308 of sheath 300 may not have sharp edges, such that distal end 308 may pass over lead body 202 of electrode lead 200 and through tissue while preventing damage to lead body 202 as sheath 300 is advanced over lead body 202. For example, distal end 308 may have a blunt and/or rounded distal edge. In some embodiments, sheath 300 may have a length such that when distal end 308 abuts collar 216, the proximal end of electrode lead 200 is exposed beyond proximal region 302 of sheath 300. Accordingly, when lead body 202 is received through sheath 300, sheath 300 provides stability to electrode lead 200 during the lead extraction process, e.g., via dilator 400 and trephine 500.

Figures 4A, 4B, 4C:
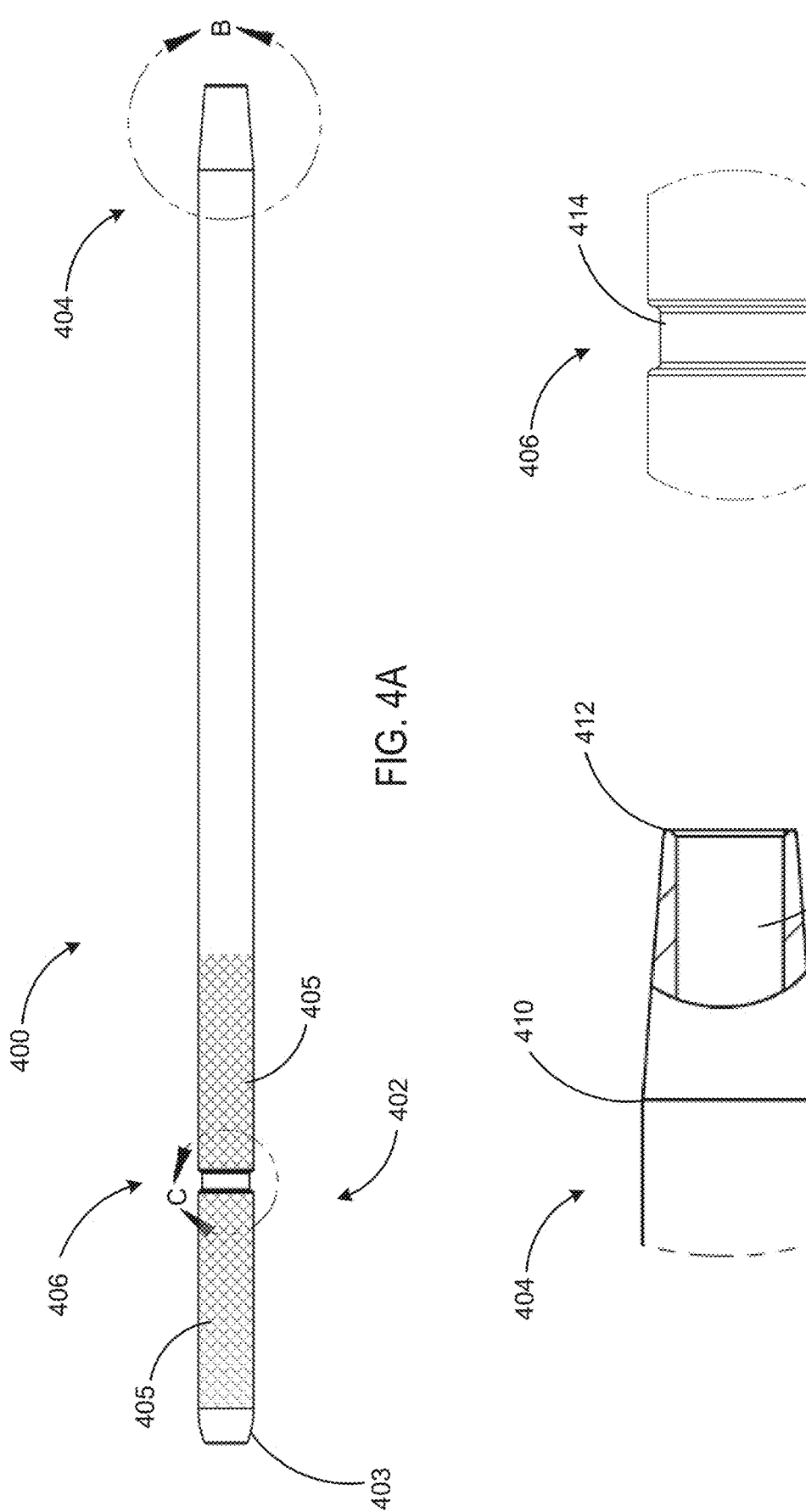
FIG. 4A illustrates an exemplary dilator of the lead extraction system of FIG. 1, constructed in accordance with the principles of the present disclosure.
FIG. 4B is a close-up view of a distal portion of the dilator of FIG. 4A.
FIG. 4C is a close-up view of an alignment marker at a proximal portion of the dilator of FIG. 4A.

Referring now to FIGS. 4A to 4C, an exemplary dilator is provided. As shown in FIG. 4A, dilator 400 includes proximal region 402 and distal region 404. The proximal end of dilator 400 at proximal region 402 may include fillet 403, which may have a curved/angled outer surface to facilitate loading of trephine 500 over the proximal end of dilator 400, as described in further detail below. For example, the cross-sectional area of the outer surface of proximal region 402 of dilator 400 may decrease in the proximal direction toward the proximal end of dilator 400 at fillet 403. In addition, dilator 400 may include alignment marker 406 to visually indicate to an operator, e.g., a surgeon, alignment of the cutting edge of trephine 500 and distal region 404 of dilator 400. As shown in FIG. 4A, at least a portion of proximal region 402 may include textured surface 405 to facilitate gripping by the surgeon during the extraction process, e.g., to advance dilator 400 distally relative to electrode lead 200 while simultaneously rotating dilator 400. For example, textured surface 405 may be debossed into the outer surface of proximal region 402 of dilator 400, e.g., via grit blasting or other machine methods known in the art. Moreover, textured surface 405 need not extend along the entire length of dilator 400. For example, textured surface 405 may extend from about an inch from the proximal end of dilator 400 to about five inches from the distal end of dilator 400. As will be understood by a person having ordinary skill in the art, textured surface 405 may extend along the outer surface of dilator 400 in any manner that permits the surgeon to effectively grip dilator 400 during the lead extraction procedure.

FIG. 4B is a close-up, partial cross-sectional view of distal region 404 of dilator 400, as indicated by circle B. Dilator 400 may be made of a rigid material, e.g., stainless steel, and have lumen 408 extending through an entire length of dilator 400. Lumen 408 is sized and shaped to receive the proximal end of sheath 300, such that dilator 400 is rotatably slidable over sheath 300. For example, the proximal end of sheath 300 may be fed through lumen 408 at distal end 412 of dilator 400, such that dilator 400 may be advanced distally relative to sheath 300 and electrode lead 200. In addition, lumen 408 is further sized and shaped to receive collar 216 and proximal fixation elements 212 in a collapsed state therethrough. Accordingly, as distal region 404 of dilator 400 is advanced distally over collar 216 and proximal fixation elements 212, distal end 412 pushes against proximal fixation elements 212 to cause proximal fixation elements 212 to transition from the expanded, deployed state to the collapsed state against lead body 202 within lumen 408 of dilator 400, thereby dislodging proximal fixation elements 212 from the surrounding tissue. In some embodiments, sheath 300 may not be used during the lead extraction process, and accordingly, lumen 408 may be sized and shaped to receive the proximal end of electrode lead 200 directly, as well as collar 216 and proximal fixation elements 212.

As shown in FIG. 4B, distal region 404 of dilator 400 may be include a chamfered taper to facilitate dilation and passage of dilator 400 through tissue. For example, the cross-sectional area of distal region 404 may decrease from point 410 towards distal end 412 of dilator 400, such that the chamfered region of distal region 404 is tapered at a pre-defined angle. Notably, the predefined angle of the chamfered region of distal region 404 is not too large so as to not damage electrode lead 200 as dilator 400 is advanced over electrode lead 200, and to maintain enough line contact with the inner surface of trephine 500 so that the cutting edge of trephine 500 only interacts with tissue at the very distal end of dilator 400, as described in further detail below. The chamfered taper of distal region 404 is readably and noticeably distinguishable from curved fillet 403 of proximal region 402 by a surgeon, such that the surgeon will immediately know which orientation dilator 400 must be in to feed the proximal end of sheath 300 and/or electrode lead 200 through distal end 412 of dilator 400.

FIG. 4C is a close-up, partial cross-sectional view of alignment marker 406 at proximal region 402 of dilator 400, as indicated by circle C. The textured surface of proximal region 402 of dilator 400 is omitted for brevity. Alignment marker 406 is used to visually indicate when the cutting edge of trephine 500 is aligned with distal region 404 of dilator 400, e.g., with point 410 of dilator 400 or distal end 412 of dilator 400, such that the surgeon will know when further distal movement of trephine 500 relative to dilator 400 will begin cutting tissue. As shown in FIG. 4C, alignment marker 406 may include groove 414 extending circumferentially about an outer surface of dilator 400. Accordingly, alignment marker 406 may visually indicate alignment between the cutting edge of trephine 500 and distal region 404 of dilator 400 when the proximal end of trephine 500 is aligned with groove 414. Alternatively, rather than a groove, a smooth section between textured sections may be used.

Figures 4D, 4E:
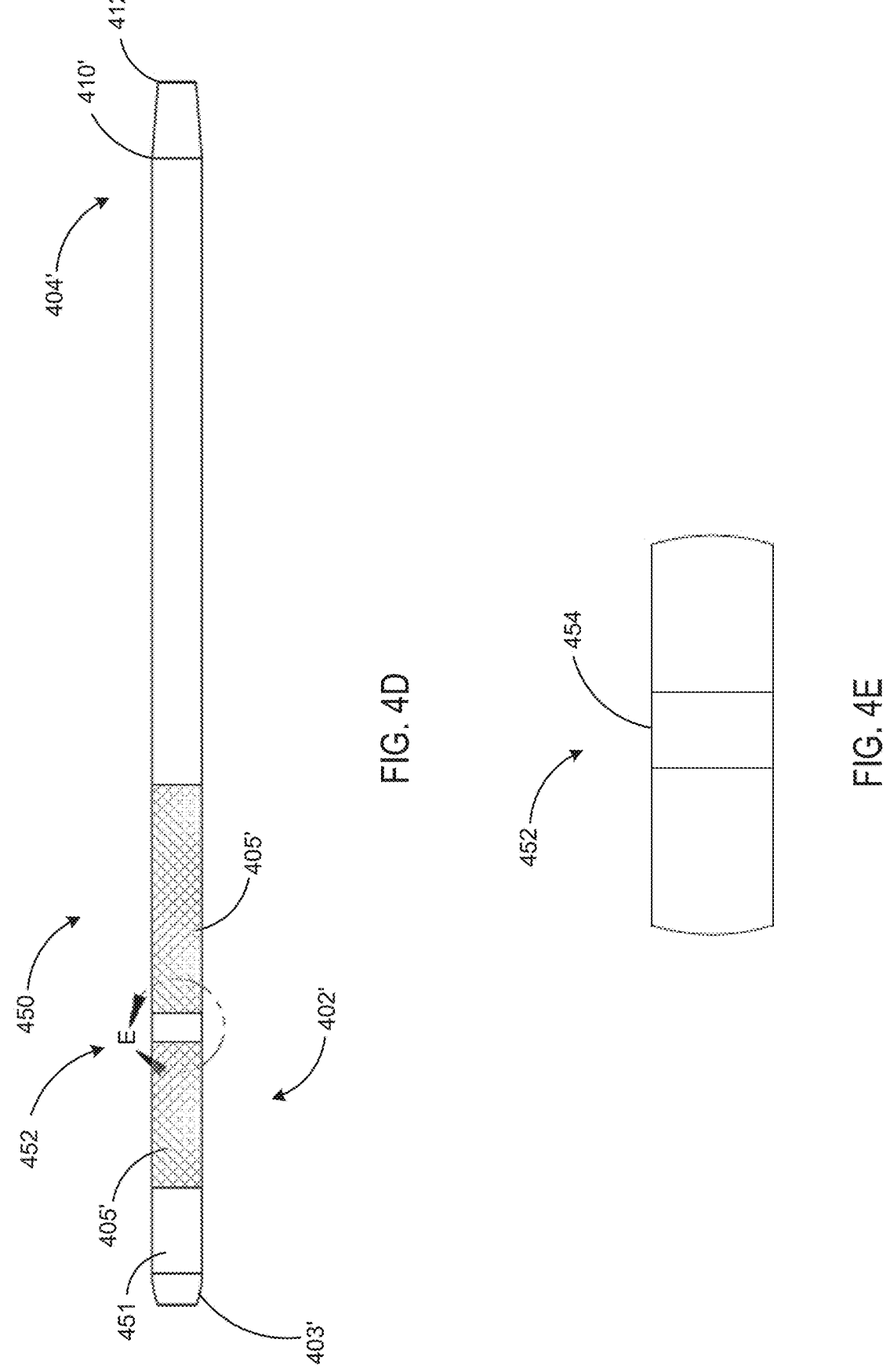
FIG. 4D illustrates an alternative exemplary dilator constructed in accordance with the principles of the present disclosure.
FIG. 4E is a close-up view of an alignment marker at a proximal portion of the dilator of FIG. 4D.

Referring now to FIGS. 4D and 4E, an alternative exemplary dilator is provided. Dilator 450 may be constructed similar to dilator 400 with similar components having like-prime reference numerals. For example, proximal region 402', fillet 403', distal region 404', textured surfaces 405', point 410', and distal end 412' correspond with proximal region 402, fillet 403, distal region 404, textured surfaces 405, point 410, and distal end 412. Dilator 450 differs from dilator 400 in that dilator 450 includes alignment marker 452, as described in further detail below with regard to FIG. 4E. Additionally, dilator 450 also may include smooth section 451, e.g., a non-textured surface, extending proximally from textured surface 405' to fillet 403', as shown in FIG. 4D.

FIG. 4E is a close-up, partial cross-sectional view of alignment marker 452 at proximal region 402' of dilator 450, as indicated by circle E. The textured surface of proximal region 402' of dilator 450 is omitted for brevity. Alignment marker 452 is used to visually indicate when the cutting edge of trephine 500 is aligned with distal region 404' of dilator 450, e.g., with point 410' of dilator 450 or distal end 412' of dilator 450, such that the surgeon will know when further distal movement of trephine 500 relative to dilator 450 will begin cutting tissue. As shown in FIG. 4E, alignment marker 452 may include smooth section 454 extending between textured surfaces 405' of dilator 450. Accordingly, alignment marker 452 may visually indicate alignment between the cutting edge of trephine 500 and distal region 404' of dilator 450 when the proximal end of trephine 500 is aligned with smooth section 454.

Figures 5A, 5B, 5C, 5D:
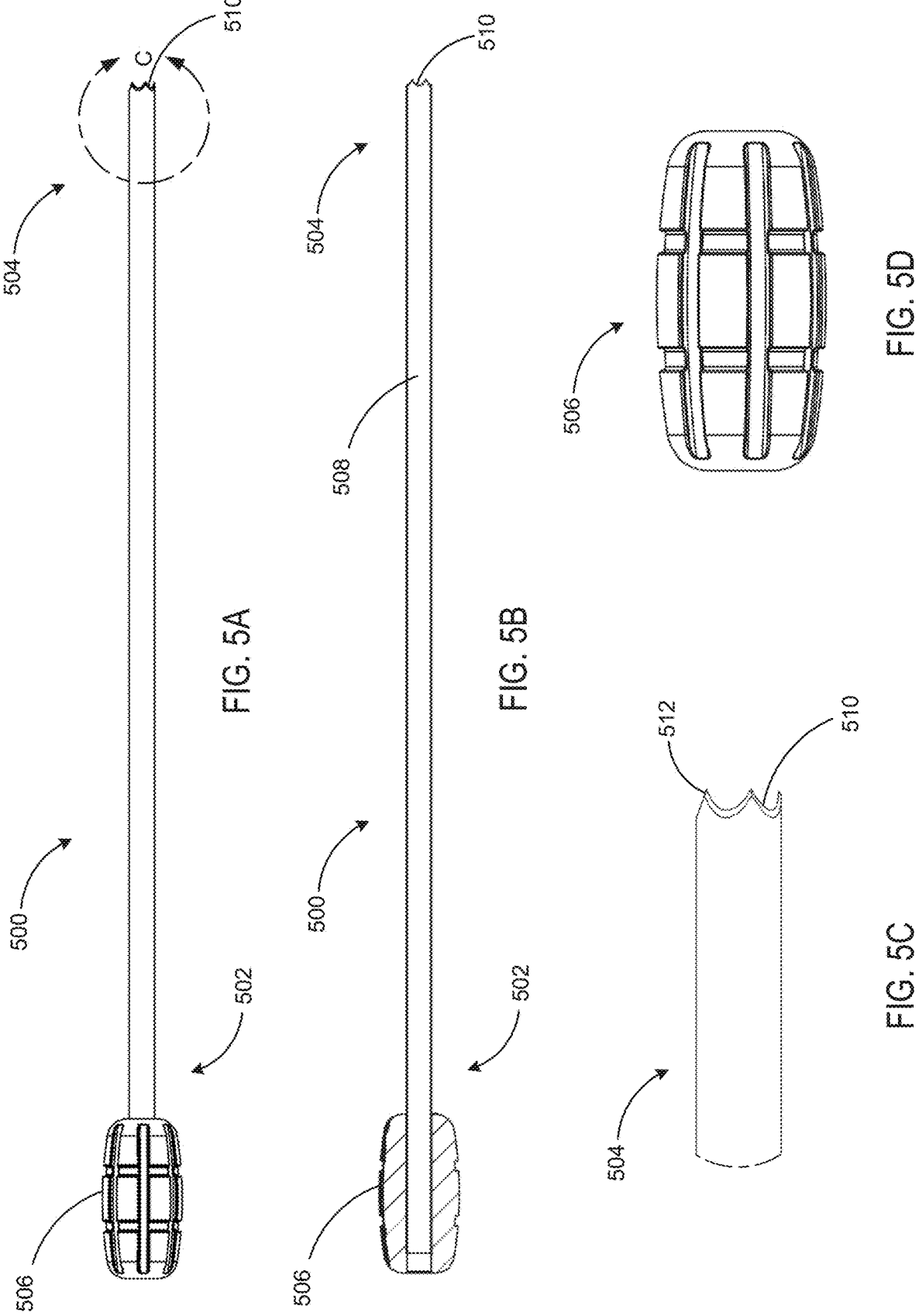
FIG. 5A illustrates an exemplary trephine of the lead extraction system of FIG. 1, constructed in accordance with the principles of the present disclosure.
FIG. 5B is a cross-sectional view thereof.
FIG. 5C is a close-up view of a distal portion of the trephine of FIG. 5A.
FIG. 5D illustrates a handle at a proximal portion of the trephine of FIG. 5A.

Referring now to FIGS. 5A to 5D, an exemplary trephine is provided. As shown in FIG. 5A, trephine 500 includes proximal region 502 which may include handle 506, and distal region 504 having cutting edge 510. FIG. 5B is a cross-sectional view of trephine 500. Trephine 500 may be made of a rigid material, e.g., stainless steel, and have lumen 508 extending through an entire length of trephine 5000. Lumen 508 is sized and shaped to receive the proximal end of dilator 400, such that trephine 500 is rotatably slidable over dilator 400. For example, the proximal end of dilator 400 may be fed through lumen 508 of trephine 500, such that trephine 500 may be advanced distally relative to dilator 400, sheath 300, and electrode lead 200. In addition, lumen 508 is further sized and shaped to receive distal fixation elements 214 in a collapsed state therethrough.

FIG. 5C is a close-up, partial cross-sectional view of distal region 504 of trephine 500, as indicated by circle C. As shown in FIG. 5C, cutting edge 510 of trephine 500 may include a plurality of proximally extending concave edges circumferentially disposed along a distal end of trephine 500. For example, cutting edge 510 of trephine 500 may include a plurality of C-shapes circumferentially arranged around the distal end such that the corresponding ends of each C-shape meets with an adjacent C-shape, e.g., forming a point at the apex. As such, the conjoining of adjacent C-shapes forms a pointed edge shape. Moreover, cutting edge 510 may include an angled surface 512, e.g., a blade, extending from the outer surface of trephine 500 towards the inner surface of trephine 512 at the distal end of trephine 500 to facilitate cutting of surrounding tissue by axially and rotational movement of trephine 500. For example, the cross-sectional area of trephine 500 may decrease toward the distal end of trephine 500 at cutting edge 510. Cutting edge 510 is sufficiently sharp to cut tissue, e.g., tissue surrounding distal fixation elements 214 of electrode lead 200, to thereby dislodge electrode lead 200 from the surrounding tissue. Cutting edge 510 further may be sharp enough to cut at least a portion of distal fixation elements 214 as trephine is rotatably advanced distally over distal fixation elements 214, such that the remainder of distal fixation elements 214 are disposed within lumen 508 of trephine 500. Alternatively, trephine 500 may include a plurality of proximally extending V-shaped edges circumferentially disposed along a distal end of trephine 500. As will be understood by a person having ordinary skill in the art, cutting edge 510 may be formed of other shapes for safely and effectively cutting tissue and at least a portion of distal fixation elements 214.

FIG. 5D illustrates handle 506 at proximal region 502 of trephine 500. Handle 506 may include a textured surface to facilitate gripping by the surgeon during the lead extraction procedure, e.g., to advance trephine 500 distally relative to dilator 400 and electrode lead 200 while simultaneously rotating trephine 500. As described above, alignment of trephine 500 with the distal end of dilator 400 may be visually indicated by aligning the proximal end of trephine 500, e.g., the proximal end of handle 506, with alignment mark 406.

Figure 6:
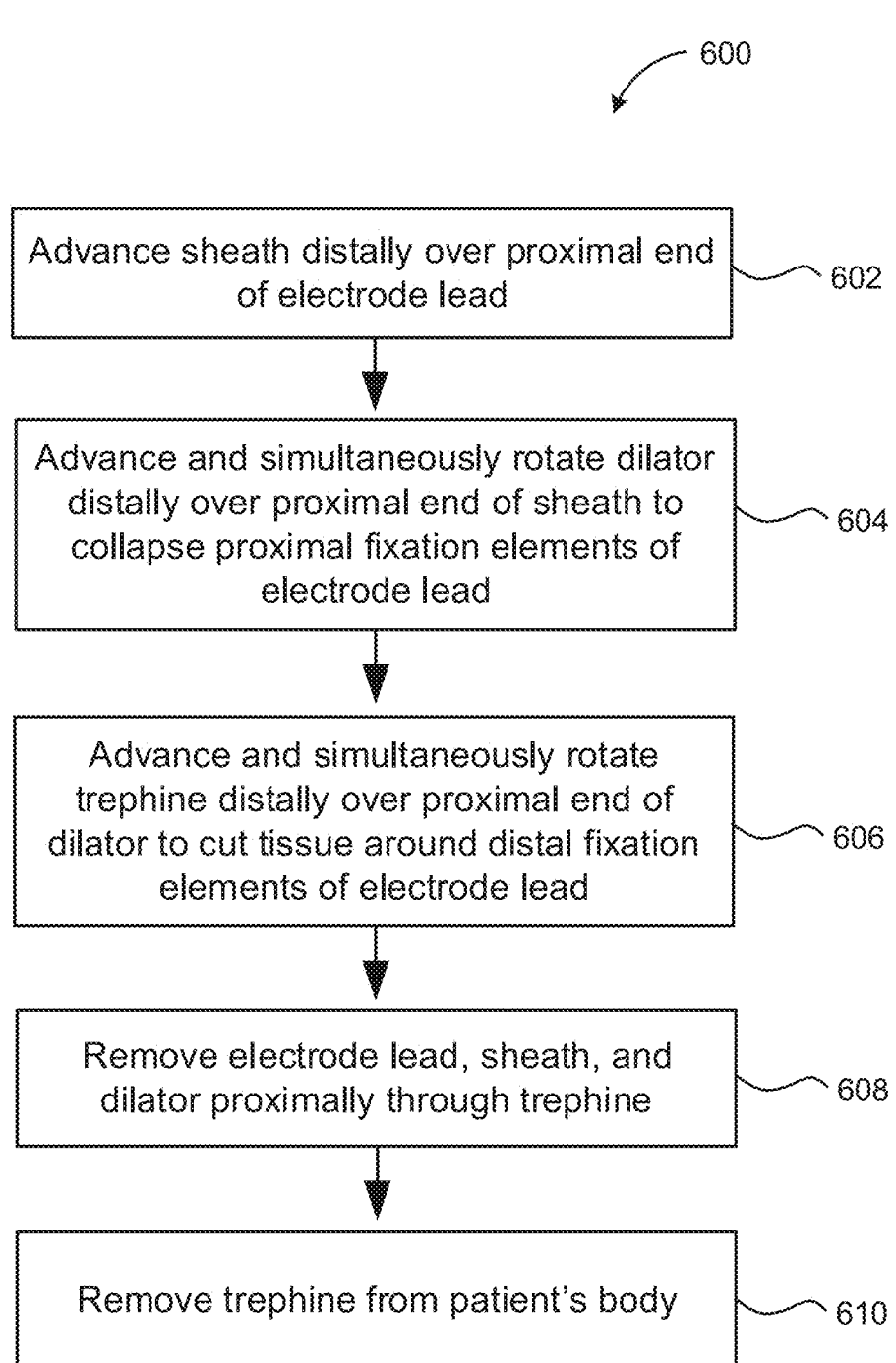
FIG. 6 is a flow chart of exemplary method steps for extracting an implanted electrode lead in accordance with the principles of the present disclosure.
Figure 7A:
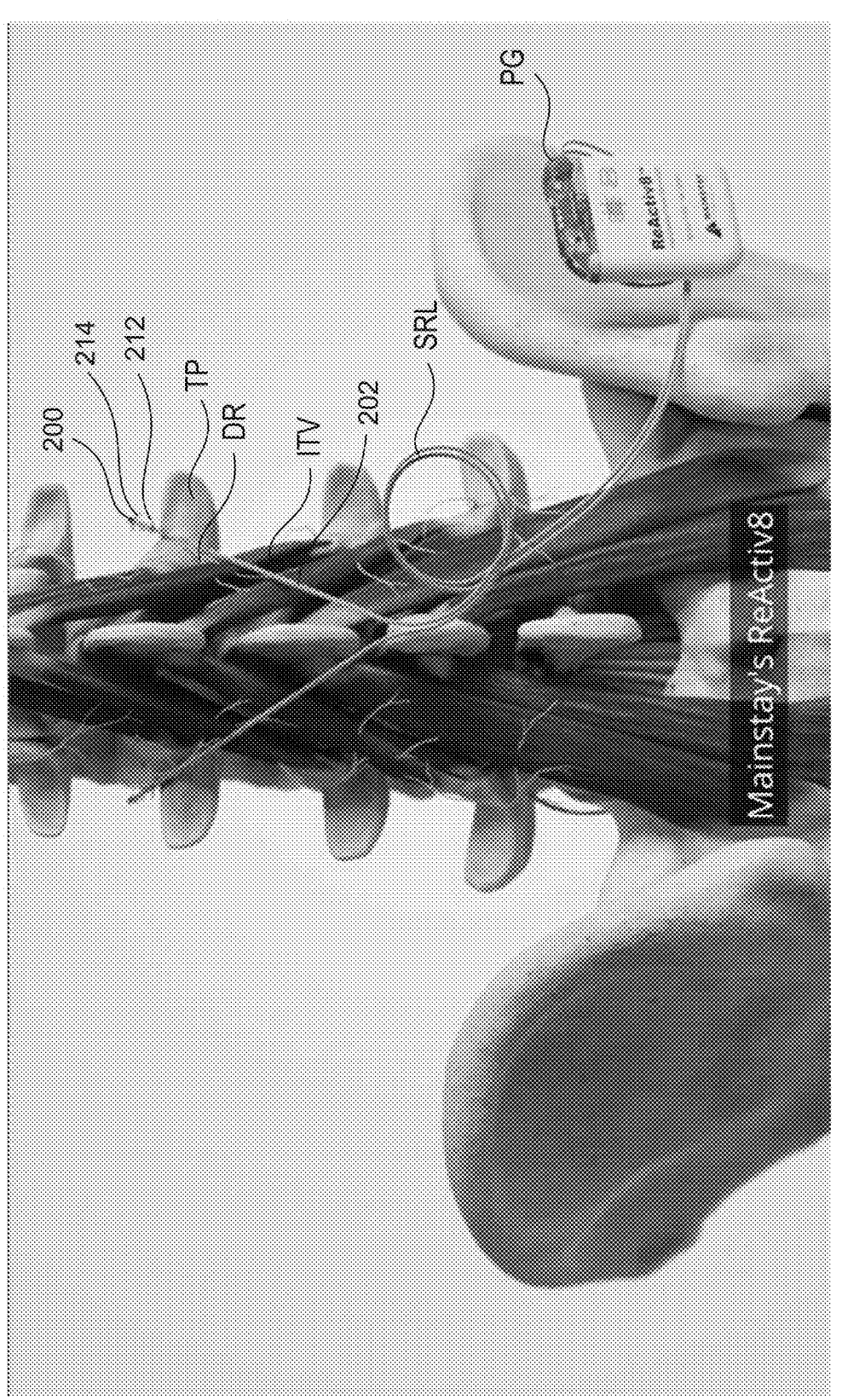
FIGS. 7A to 7I illustrate exemplary method steps for extracting an implanted electrode lead in accordance with the principles of the present disclosure.

Referring now to FIG. 6, an exemplary method for extracting implanted electrode lead 200 using system 100 is provided. Some of the steps of method 700 may be further elaborated by referring to FIGS. 7A to 7I. Initially, as shown in FIG. 7A, one or more electrode leads 200 may be coupled to pulse generator PG for providing electrostimulation therapy to tissue associated with one or more spine stabilizing muscles associated with local segmental control of a lumbar spine within a back of a patient. Illustratively, FIG. 7A shows the ReActiv8® system available from Mainstay Medical Limited of Dublin, Ireland. As shown in FIG. 7A, pulse generator PG may be implanted in the patient, e.g., an implantable pulse generator (IPG), within the lower back of the patient such that electrode lead 200 is fully implanted. Alternatively, pulse generator PG may be worn externally by the patient, such that electrode lead 200 is partially implanted and extends from pulse generator PG percutaneously toward the target stimulation site. Either way, the target stimulation site may be above traverse process TP adjacent to dorsal root DR within the plane of intertransversarii ITV, along the patient's spinal column in the lumbar region.

Pulse generator PG is configured to generate pulses such that electrodes 204, 206, 208, 210 deliver neuromuscular electrical stimulation ("NMES") to target tissue. In one embodiment, the electrodes are positioned to stimulate a peripheral nerve where the nerve enters skeletal muscle, which may be one or more of the multifidus, transverse abdominus, quadratus lumborum, psoas major, internus abdominus, obliquus externus abdominus, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain.

Exemplary stimulation parameters in accordance with aspects of the present disclosure are now described. Preferably, such stimulation parameters are selected and programmed to induce contraction of muscle to restore neural control and rehabilitate muscle associated with control of the spine, thereby improving lumbar spine stability and reducing back pain. As used in this specification, "to restore muscle function" means to restore an observable degree of muscle function as recognized by existing measures of patient assessment, such as the Oswestry Disability Index ("ODI") as described in Lauridsen et al., *Responsiveness and minimal clinically important difference for pain and disability instruments in low back pain patients*, BMC Musculoskeletal Disorders, 7: 82-97 (2006), the European Quality of Life Assessment 5D ("EQ-5D") as described in Brazier et al., *A comparison of the EQ-5D and SF-6D across seven patient groups*, Health Econ. 13: 873-884 (2004), or a Visual Analogue Scale ("VAS") as described in Hagg et al., *The clinical importance of changes in outcome scores after treatment for chronic low back pain*, Eur Spine J 12: 12-20 (2003). In accordance with one aspect of the present disclosure, "to restore muscle function" means to observe at least a 15% improvement in one of the foregoing assessment scores within 30-60 days of initiation of treatment. The stimulation parameters may be programmed into pulse generator PG, and/or may be adjusted in the pulse generator 300 responsive to (i) stimulation commands transferred from the activator or (ii) programming data transferred from the external programmer.

The stimulation parameters include, for example, pulse amplitude (voltage or current), pulse width, stimulation rate, stimulation frequency, ramp timing, cycle timing, session timing, and electrode configuration, including commands to start or stop a treatment session. In one embodiment, pulse amplitude is programmed to be adjustable between 0 and 7 mA. In a preferred embodiment, pulse amplitude is programmed to be between about 2-5 mA, 2.5-4.5 mA, or 3-4 mA, and preferably about 3.5 mA. In one embodiment, pulse width is programmed to be adjustable between 25 and 500 μs. In a preferred embodiment, pulse width is programmed to be between about 100-400 μs, 150-350 μs, or 200-300 μs, and preferably about 350 μs. In one embodiment, stimulation rate is programmed to be adjustable between 1 and 40 Hz. In a preferred embodiment, stimulation rate is programmed to be between about 5-35 Hz, 10-30 Hz, or 15-20 Hz, and preferably about 20 Hz. In one embodiment, on ramp timing is programmed to be adjustable between 0 and 5 s. In a preferred embodiment, on ramp timing is programmed to be between about 0.5-4.5 s, 1-4 s, 1.5-3.5 s, or 2-3 s, and preferably about 2.5 s. In one embodiment, off ramp timing is programmed to be adjustable between 0 and 5 s. In a preferred embodiment, off ramp timing is programmed to be between about 0.5-4.5 s, 1-4 s, 1.5-3.5 s, or 2-3 s, and preferably about 2.5 s. In one embodiment, cycle-on timing is programmed to be adjustable between 2 and 20 s. In a preferred embodiment, cycle-on timing is programmed to be between about 4-18 s, 6-16 s, 8-14 s, 9-13 s, or 10-12 s and preferably about 10 s. In one embodiment, cycle-off timing is programmed to be adjustable between 20 and 120 s. In a preferred embodiment, cycle-off timing is programmed to be between about 30-110 s, 40-100 s, 50-90 s, 55-85 s, 60-80 s, or 65-75 s and preferably about 70 s. In one embodiment, session timing is programmed to be adjustable between 1 and 60 min. In a preferred embodiment, session timing is programmed to be between about 5-55 min, 10-50 min, 15-45 min, 20-40 min, or 25-35 min, and preferably about 30 min.

Figure 7B:
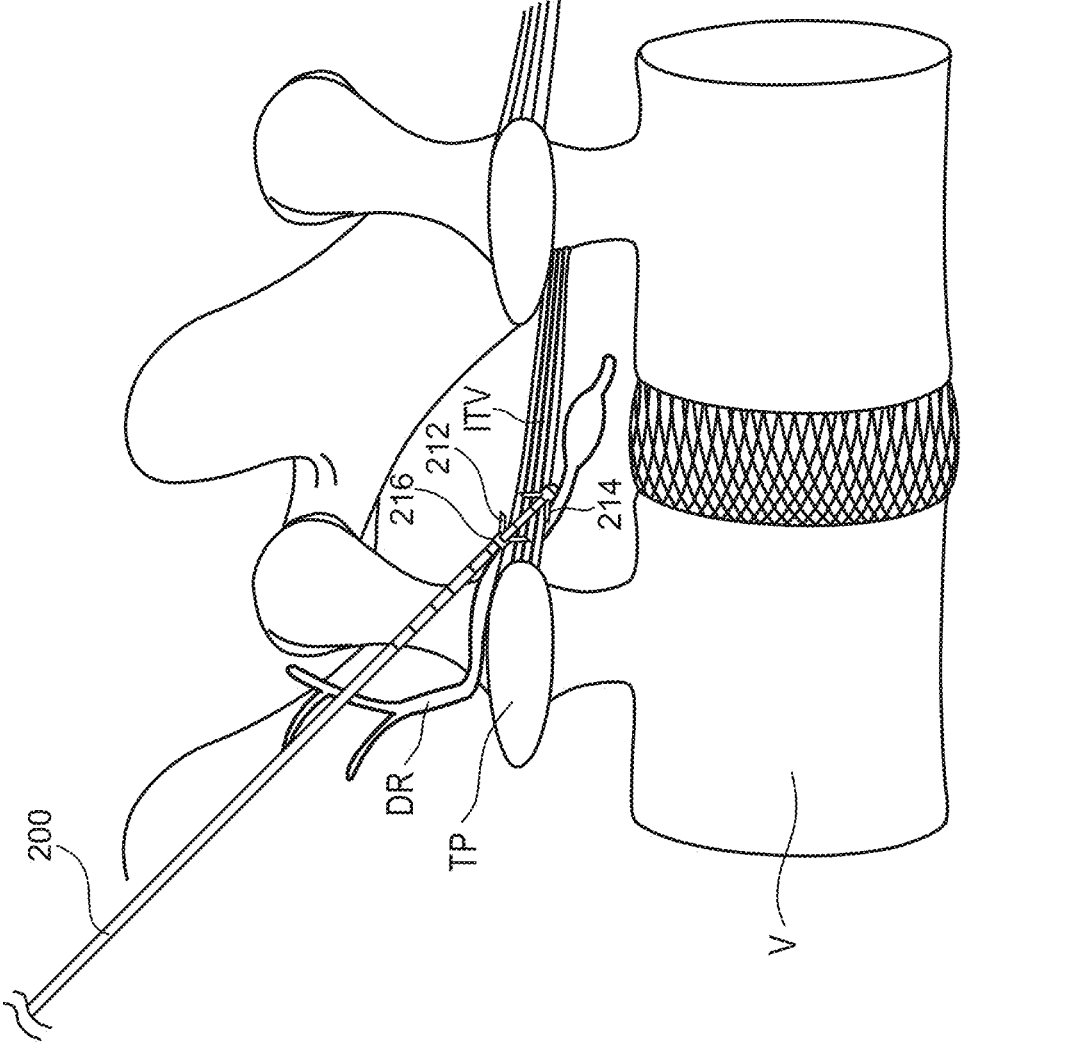

As shown in FIG. 7A, electrode lead 200 may include strain relief loop SRL for reducing axial forces on proximal and distal fixation elements 212, 214 of electrode lead 200, as described in U.S. Pat. No. 10,195,419 to Shiroff, assigned to the assignee of the present disclosure, and incorporated herein in its entirety by reference. In order to begin the extraction procedure of electrode lead 200 from the patient, an incision is first made adjacent to the connection of electrode lead 200 and pulse generator PG, and the proximal end of electrode lead 200 is decoupled from pulse generator PG such that the proximal end of electrode lead 200 is exposed from the patient, as shown in FIG. 7B. When pulse generator PG is worn externally by the patient, the proximal end of electrode lead 200 may be decoupled from pulse generator PG external to the patient, and an incision may be made adjacent to the entry point of electrode lead 200 into the patient to permit percutaneous passage of lead extraction system 100.

Figure 7C:
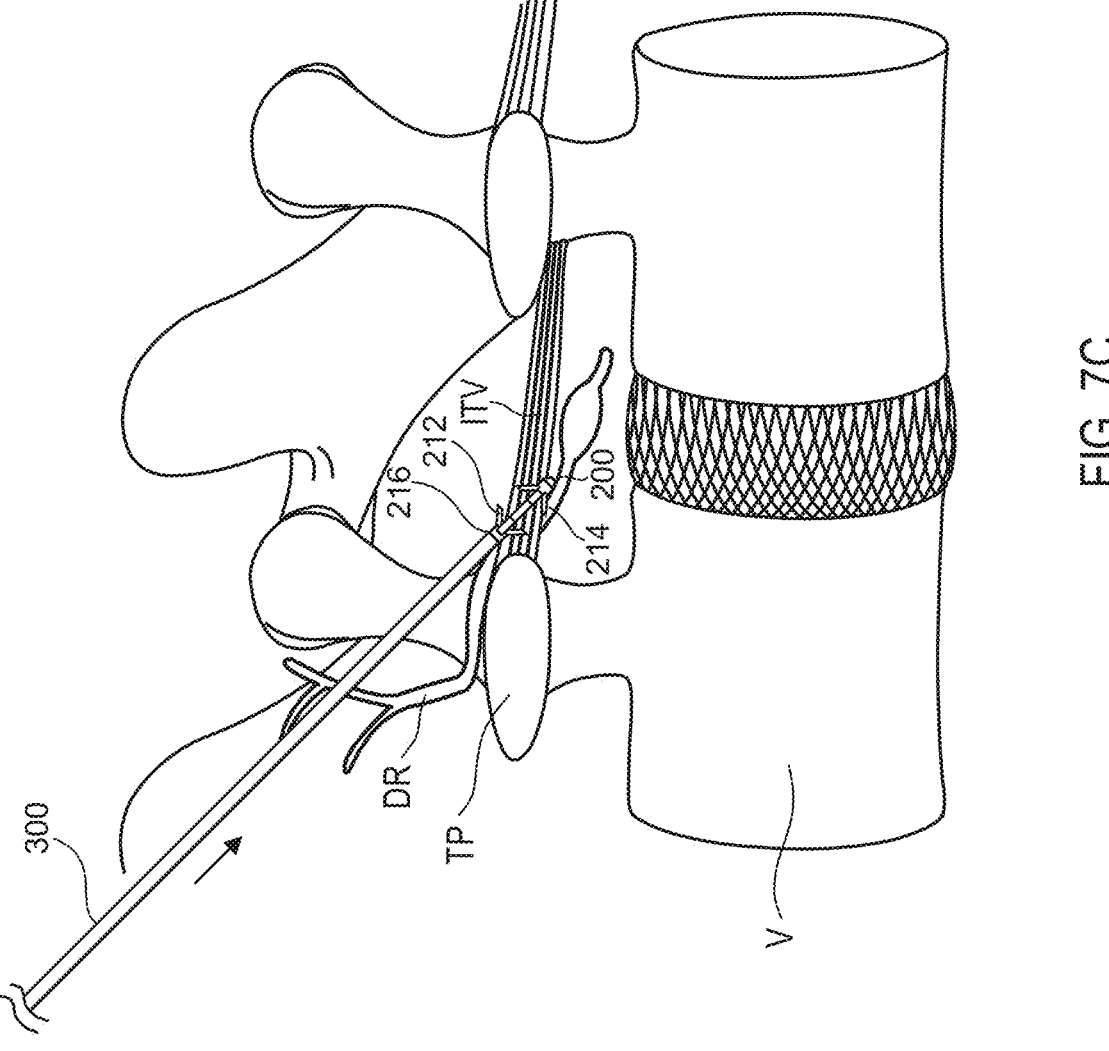
Figure 7D:
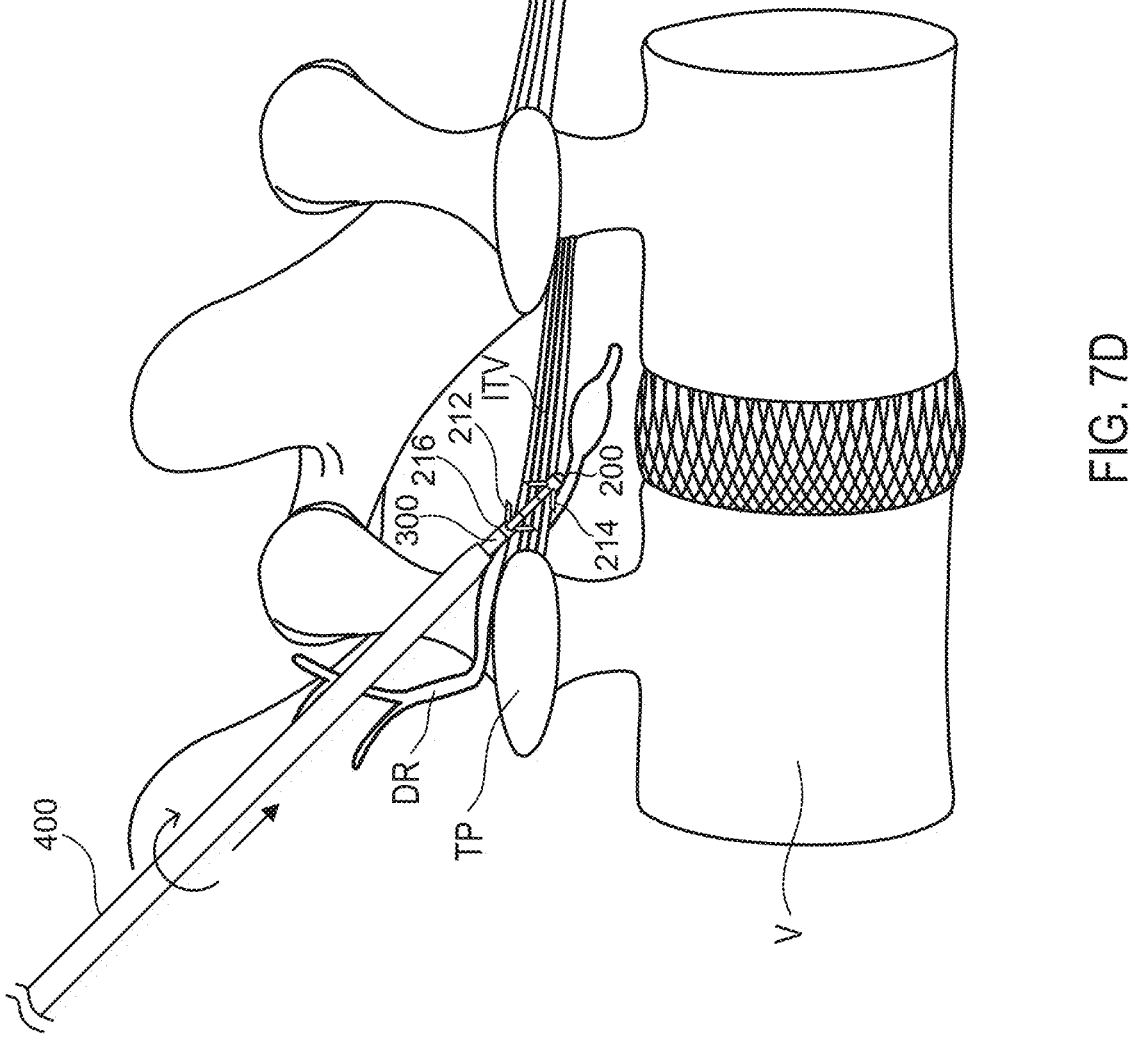
Figure 7E:
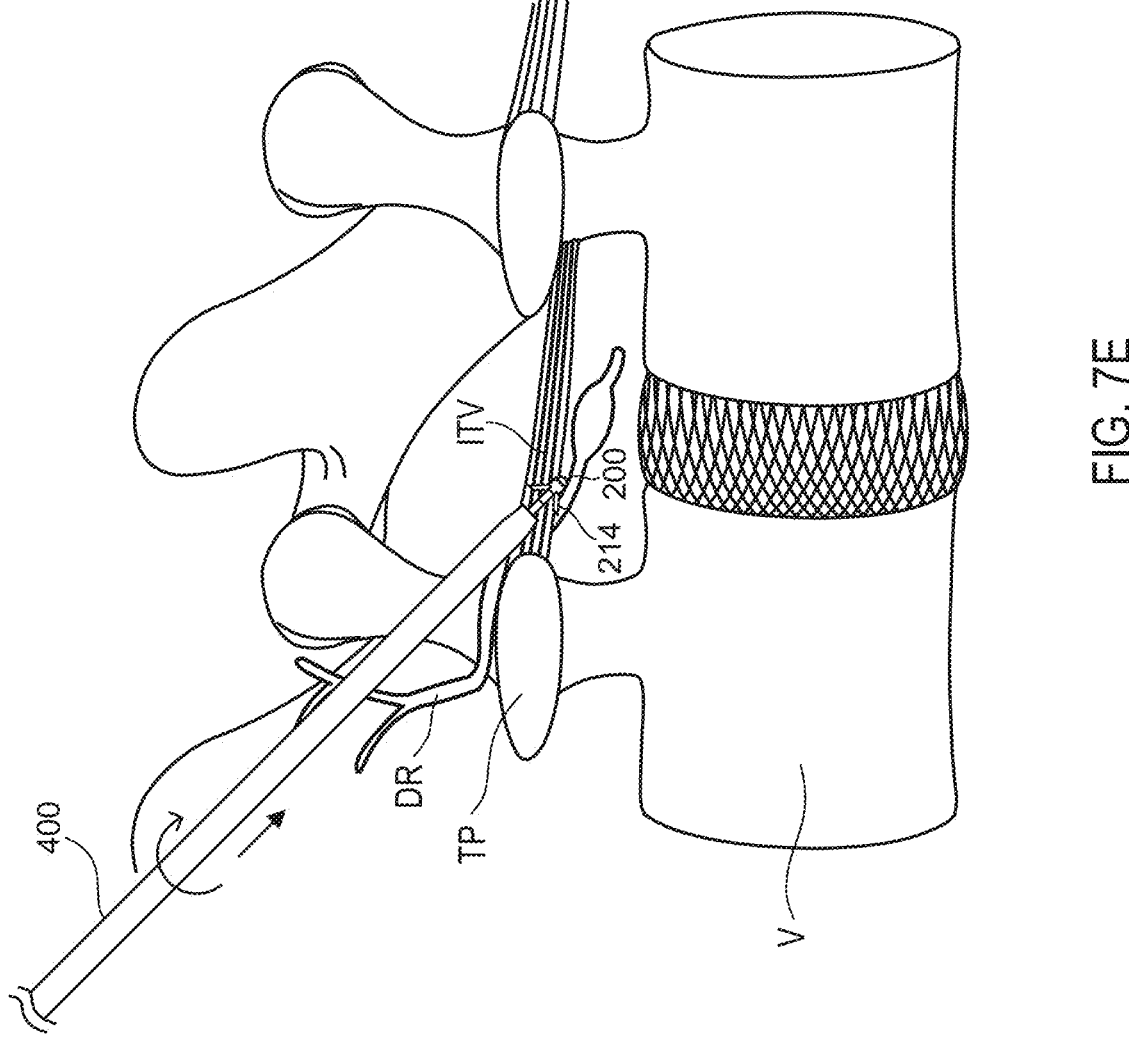

At step 602, the proximal end of electrode lead 200 may be fed through lumen 306 of sheath 300 such that sheath 300 may be advanced distally relative to electrode lead 200 until the distal end of sheath 300 abuts collar 216 of electrode lead 200, as shown in FIG. 7C. At step 604, the proximal end of sheath 300 and electrode lead 200 may be fed through lumen 408 of dilator 400, such that dilator 400 may be advanced distally while simultaneously rotated along sheath 300, as shown in FIG. 7D. As shown in FIG. 7E, dilator 400 may be rotatably and axially advanced distally relative to electrode lead 200 until distal end 412 contacts and causes proximal fixation elements 212 of electrode lead 200 to transition to its collapsed configuration toward lead body 202 of electrode lead 200 within lumen 408 of dilator 400. Successful collapse of proximal fixation elements 212 within dilator 400 may be observed via, e.g., fluoroscopy. As described above, in some embodiments, sheath 300 does not need to be advanced over electrode lead 200, and thus, the proximal end of electrode lead 200 may be fed directly into lumen 408 of dilator 400, such that dilator 400 may be rotatably and axially advanced directly over electrode lead 200 until distal end 412 of dilator 400 collapses proximal fixation elements 212 of electrode lead 200, as shown in FIG. 7E.

Figure 7F:
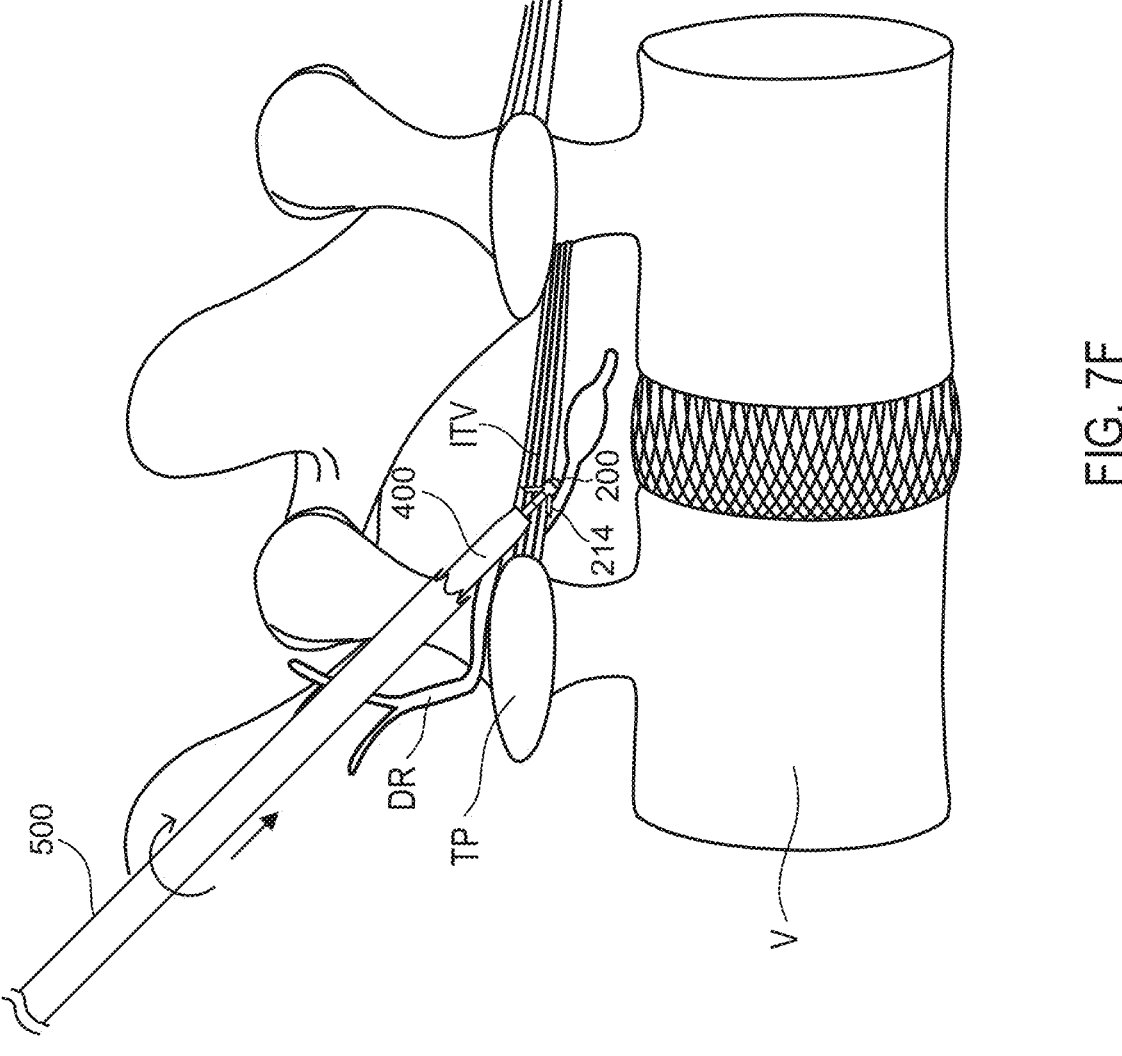

At step 606, the proximal end of dilator 400, sheath 300, and electrode lead 200 may be fed through lumen 508 of trephine 500, such that trephine 500 may be advanced distally while simultaneously rotated along dilator 400, as shown in FIG. 7F. By observing when the proximal end of trephine 500, e.g., the proximal end of handle 506, is aligned with alignment marker 406 of dilator 400, the surgeon may know when cutting edge 510 is aligned with the distal end of dilator 400 such that further axially movement of trephine 500 relative to dilator 400 will begin cutting tissue surrounding the distal region of electrode lead 200.

Figure 7G:
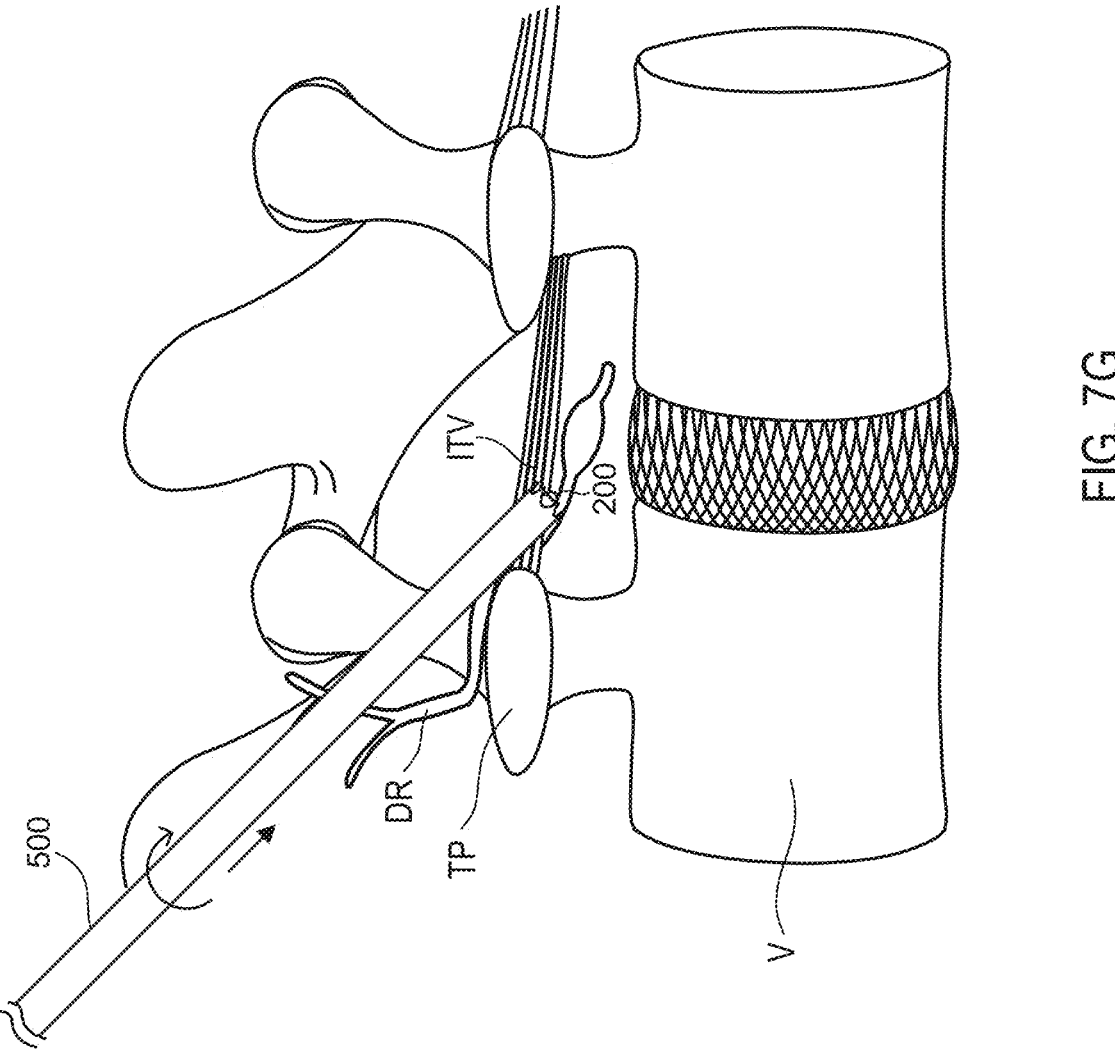

As shown in FIG. 7G, trephine 500 may be rotatably and axially advanced distally relative to dilator 400 and electrode lead 200 beyond distal end 412 of dilator 400 such that cutting edge 510 of trephine 500 cuts tissue surrounding distal fixation elements 214. As described above, cutting edge 510 may also cut at least a portion of distal fixation elements 214 as cutting edge 510 is rotatably and axially advanced over distal fixation elements 214. Trephine 500 may be rotatably and axially advanced relative to electrode lead 200 until distal fixation elements 214, or what remains of distal fixation elements 214, is disposed within lumen 508 of trephine 500. Successful collapse of distal fixation elements 214 within trephine 500 may be observed via, e.g., fluoroscopy.

Figure 7H:
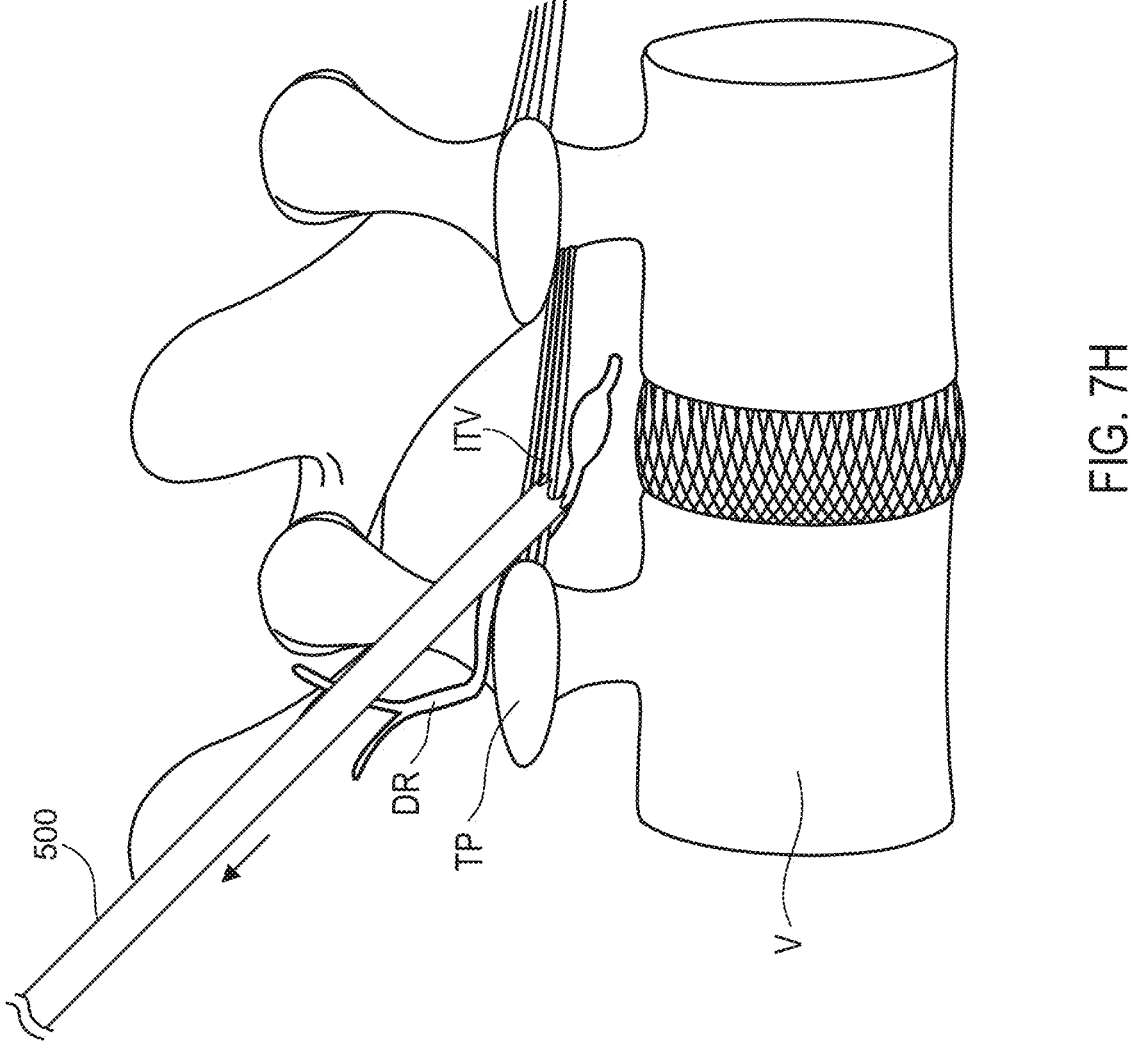
Figure 7I:
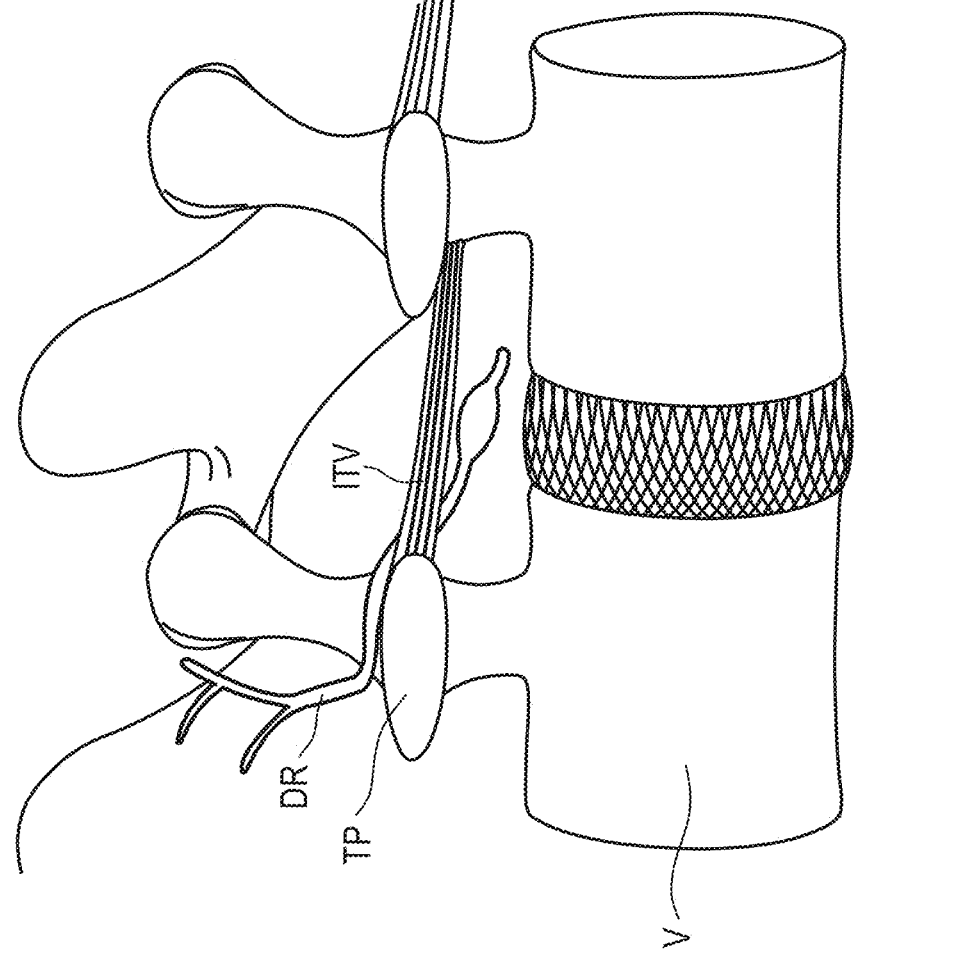

At step 608, electrode lead 200, sheath 300 (if used), and dilator 400 may be removed from the patient by being retracted proximally through lumen 508 of trephine 500, as shown in FIG. 7H. At step 610, trephine 500 may be removed from the patient's body as shown in FIG. 7I.

While various illustrative embodiments of the disclosure are described above, it will be apparent to one skilled in the art that various changes and modifications may be made therein without departing from the disclosure. For example, system 100 may be used to extract various types of neuromodulation leads, e.g., leads implanted for peripheral neuromodulation or leads used for spinal cord stimulation, as well as leads implanted in other parts of the body other than the lower back, e.g., in peripheral musculoskeletal, fascial, or visceral areas of the body. Further, system 100 may be used to extract neuromodulation leads having various fixation element configurations, e.g., single or multiple fixation elements such as tines, hooks, barbs, coils, etc., as well as fixation elements extending from the lead body at various angles, e.g., proximally extending, distally extending, perpendicular, or any combination thereof. The appended claims are intended to cover all such changes and modifications that fall within the true scope of the disclosure.

What is claimed:

1. A system for extracting an electrode lead comprising an implanted fixation element, the system comprising:

an electrode lead comprising a fixation element configured to anchor the electrode lead in or adjacent to tissue associated with one or more spine stabilizing muscles associated with local segmental control of a lumbar spine within a back of a patient;

a dilator having a lumen sized and shaped to receive a proximal end of the electrode lead therethrough such that the dilator is slideable along the electrode lead, a distal portion of the dilator configured to be advanced distally to separate tissue surrounding the electrode lead; and a trephine having a lumen sized and shaped to receive a proximal end of the dilator therethrough, a distal portion of the trephine comprising a cutting edge configured to be advanced distally to cut tissue surrounding the fixation element to thereby dislodge the electrode lead.

2. The system of claim 1, wherein the distal portion of the dilator is configured to be advanced distally to collapse proximal fixation elements of the fixation element within the lumen of the dilator, and wherein the cutting edge of the trephine is configured to be advanced distally to cut tissue surrounding distal fixation elements of the fixation element to thereby dislodge the electrode lead.

3. The system of claim 2, further comprising:

a sheath having a lumen sized and shaped to receive a proximal end of the electrode lead therethrough such that the sheath is slideable along the electrode lead, a distal portion of the sheath configured to be advanced distally until it abuts a collar on the electrode lead that is coupled to the proximal fixation elements, thereby preventing further distal advancement of the sheath relative to the electrode lead, wherein the lumen of the dilator is sized and shaped to receive a proximal end of the sheath therethrough such that the dilator is slideable along the sheath.

4. The system of claim 3, wherein the sheath comprises an outer diameter substantially equal to an outer diameter of the collar.

5. The system of claim 2, wherein the dilator is configured to be rotated as the distal portion of the dilator is advanced distally to collapse the proximal fixation elements within the lumen of the dilator.

6. The system of claim 1, wherein the distal portion of the dilator is tapered.

7. The system of claim 6, wherein a cross-sectional area of the distal portion of the dilator decreases distally toward a distal end of the dilator.

8. The system of claim 1, wherein the cutting edge of the distal portion of the trephine comprises a plurality of proximally extending concave edges circumferentially disposed along a distal end of the trephine.

9. The system of claim 1, wherein the cutting edge of the distal portion of the trephine is angled to facilitate cutting of the tissue surrounding the fixation element.

10. The system of claim 1, wherein the cutting edge of the distal portion of the trephine is further configured to cut at least a portion of the fixation element.

11. The system of claim 1, wherein the trephine is configured to be rotated as the cutting edge of the trephine is advanced distally to cut tissue surrounding the fixation element.

12. The system of claim 1, wherein a proximal portion of the trephine comprises a handle configured to facilitate rotation of the trephine by a user.

13. The system of claim 1, wherein at least one of the dilator or trephine comprises a rigid material.

14. The system of claim 13, wherein the rigid material is stainless steel.

15. The system of claim 1, wherein a proximal portion of the dilator comprises one or more textured surfaces configured to facilitate gripping of the dilator.

16. The system of claim 15, wherein the dilator comprises an alignment marker disposed between two of the one or more textured surfaces, the alignment marker configured to facilitate alignment of the cutting edge of trephine and the distal portion of the dilator.

17. The system of claim 16, wherein the alignment marker comprises a groove extending circumferentially along an outer surface of the dilator.

18. The system of claim 16, wherein the alignment marker comprises a smooth section between the two of the one or more textured surfaces.

19. A method for extracting an electrode lead comprising a fixation element implanted in a patient's body, the method comprising:

advancing a dilator distally over a proximal end of the electrode lead to thereby separate tissue surrounding the electrode lead;

advancing a trephine distally over a proximal end of the dilator, such that a cutting edge at a distal portion of the trephine cuts tissue surrounding the fixation element to thereby dislodge the electrode lead; and removing the electrode lead from the patient's body.

20. The method of claim 19, wherein advancing the dilator distally over the proximal end of the electrode lead comprises advancing the dilator distally over proximal fixation elements of the fixation element to thereby collapse the proximal fixation elements within the lumen of the dilator, and wherein advancing the trephine distally over the proximal end of the dilator comprises advancing the trephine distally, such that the cutting edge of the trephine cuts tissue surrounding distal fixation elements of the fixation element to thereby dislodge the electrode lead.

21. The method of claim 20, further comprising:

prior to advancing the dilator distally over the proximal end of the electrode lead, advancing a sheath distally over a proximal end of the electrode lead until a distal end of the sheath abuts a collar of the proximal fixation elements, wherein advancing the dilator distally over the proximal end of the electrode lead comprises advancing the dilator distally over the proximal end of the sheath.

22. The method of claim 19, wherein advancing the dilator distally over the proximal end of the electrode lead comprises rotating the dilator as the dilator is advanced distally.

23. The method of claim 19, wherein advancing the trephine distally comprises rotating the trephine as the trephine is advanced distally to cut the tissue surrounding the fixation element.

24. The method of claim 19, further comprising cutting at least a portion of the fixation element by advancing the trephine distally over the fixation element to facilitate dislodgement of the electrode lead.

25. The method of claim 19, further comprising:

removing the electrode lead and dilator proximally through the lumen of the trephine; and removing the trephine from the patient's body.

26. A system for extracting an electrode lead comprising an implanted fixation element, the system comprising:

a dilator having a lumen sized and shaped to receive a proximal end of the electrode lead therethrough such that the dilator is slideable along the electrode lead, a distal portion of the dilator configured to be advanced distally to separate tissue surrounding the electrode lead, wherein the distal portion of the dilator is configured to be advanced distally to collapse proximal fixation elements of the fixation element within the lumen of the dilator; and a trephine having a lumen sized and shaped to receive a proximal end of the dilator therethrough, a distal portion of the trephine comprising a cutting edge configured to be advanced distally to cut tissue surrounding distal fixation elements of the fixation element to thereby dislodge the electrode lead; and a sheath having a lumen sized and shaped to receive a proximal end of the electrode lead therethrough such that the sheath is slideable along the electrode lead, a distal portion of the sheath configured to be advanced distally until it abuts a collar on the electrode lead that is coupled to the proximal fixation elements, thereby preventing further distal advancement of the sheath relative to the electrode lead, wherein the lumen of the dilator is sized and shaped to receive a proximal end of the sheath therethrough such that the dilator is slideable along the sheath.

* * * * *